United States Patent [19]

Devine et al.

[11] Patent Number: 5,968,785
[45] Date of Patent: *Oct. 19, 1999

[54] IN VITRO TRANSPOSITION OF ARTICLE TRANSPOSONS

[75] Inventors: Scott E. Devine, Ellicott City; Jef D. Boeke; Lelita T. Braiterman, both of Baltimore, all of Md.

[73] Assignee: The Johns Hopkins University, Baltimore, Md.

[ * ] Notice: This patent is subject to a terminal disclaimer.

[21] Appl. No.: 08/796,364

[22] Filed: Feb. 6, 1997

Related U.S. Application Data

[62] Division of application No. 08/204,675, Mar. 2, 1994, Pat. No. 5,677,170.

[51] Int. Cl.$^6$ ............... C12N 15/64; C12P 19/34; C07H 21/04
[52] U.S. Cl. ............. 435/91.41; 435/91.3; 435/320.1; 536/23.7
[58] Field of Search ............... 435/91.41, 91.3, 435/320.1; 536/23.7

[56] References Cited

U.S. PATENT DOCUMENTS 5,677,170  10/1997  Devine et al. ................. 435/320.1

OTHER PUBLICATIONS

Kasai, et al., Efficient Large–Scale Sequencing of the *Escherichia coli* Genome: Implementation of a Tansposon–and PCR–Based Strategy for the Analysis of Ordered λ Phage Clones, *Nucleic Acids Research*, 20(24):6509–6515 (1992).

Phadnis, et al., Tn5supF, a 264–Base–Pair Transposon Derived from Tn5 for Insertion Mutagenesis and Sequencing DNAs Cloned in Phage λ, *Proc. Natl. Acad. Sci. USA*, 86:5908–5912 (1989).

Strathmann, et al., "Transposon–Facilitated DNA Sequencing", *Proc. Natl. Acad. Sci. USA*, 88:1247–1250 (1991).

Seifert, et al., Shuttle Mutagenesis: A Method of Transposon Mutagenesis for *Saccharomyces cerevisiae*, *Proc. Natl. Acad. Sci. USA*, 83:735–739 (1986).

Ahmed, "A Vector for Sequencing Long (40–kb) DNA Fragments", *Gene*, 75:315–321 (1988).

Way, et al., "New TN10 Derivatives for Transposon Mutagenesis and for Construction of lacA Operon Fusions by Transposition", *Gene*, 32:369–379 (1984).

Kleckner, et al., "Uses of Transposons with Emphasis of TN10", *Methods in Enzymology*, 204:139–180 (1991).

Eichinger, et al., "The DNA Intermediate in Yeast Ty1 Element Transposition Copurifies with Virus–Like Particles: Cell–Free Ty1 Transposition, "*Cell*, 54:955–966 (1988).

Brown, et al., "Correct Integration of Retroviral DNA in vitro", *Cell*, 49:347–356 (1987).

Eichinger, et al., "A Specific Terminal Structure is Required for Ty1 Transposition", *Gene & Development*, 4:324–330 (1990).

*Primary Examiner*—Nancy Degen
*Attorney, Agent, or Firm*—Banner & Witcoff, Ltd.

[57] ABSTRACT

We have developed efficient methods of creating artificial transposons and inserting these transposons into plasmid targets in vitro, primarily for the purpose of mapping and sequencing DNA. A plasmid has been engineered to convert virtually any DNA sequence, or combination of sequences, into an artificial transposon; hence, custom transposons containing any desired feature can be easily designed and constructed. Such transposons are then efficiently inserted into plasmid targets, in vitro, using the integrase activity present in yeast Ty1 virus-like particles. Primers complementary to the transposon termini can be used to sequence DNA flanking any transposon insertion.

4 Claims, 14 Drawing Sheets

*FIG. 1*
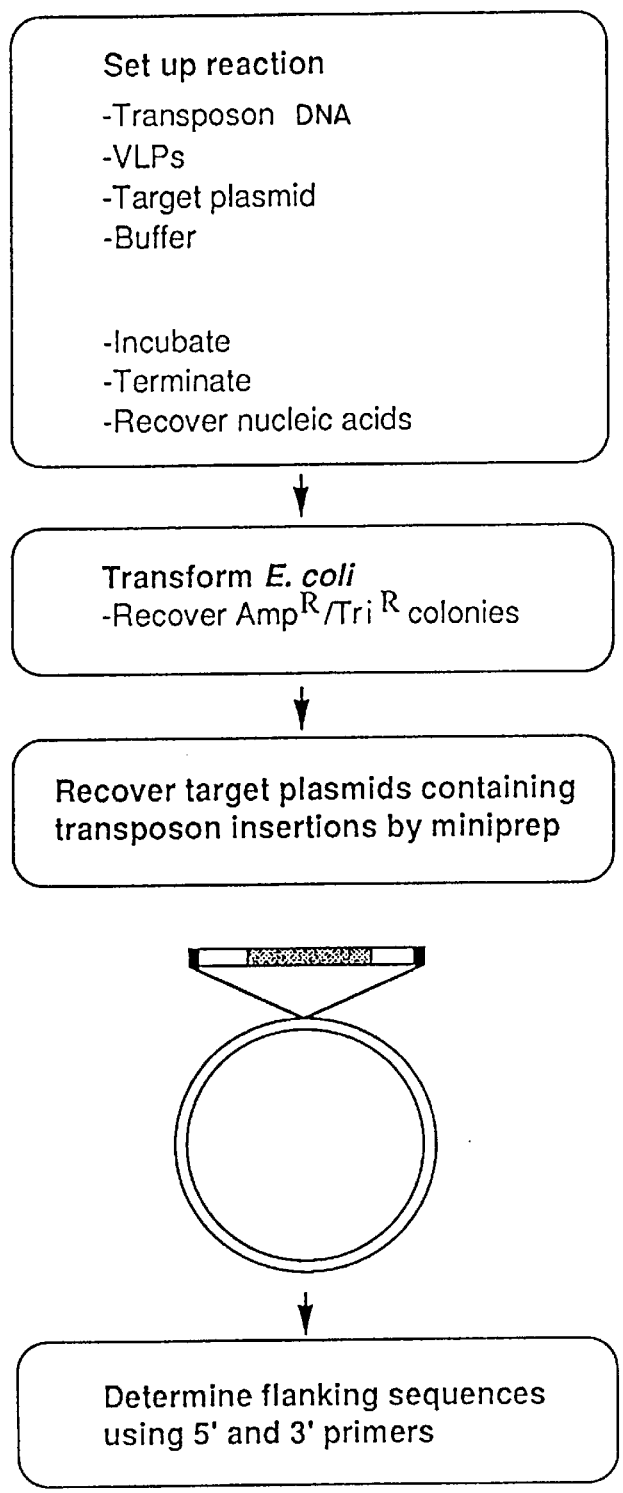
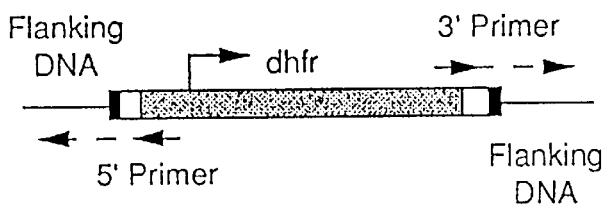

pWAFp

FIG. 8A

```
               10         20         30         40         50         60
       |          |          |          |          |          |          |
   1   TCGCGCGTTT CGGTGATGAC GGTGAAAACC TCTGACACAT GCAGCTCCCG GAGACGGTCA    60
  61   CAGCTTGTCT GTAAGCGGAT GCCGGAGCA GACAAGCCCG TCAGGGGCG TCAGGGGTG   120
 121   TTGGCGGGTG TCGGGGCTGG CTTAACTATG CGGCATCAGA GCAGATTGTA CTGAGAGTGC  180
 181   ACCATACCAC AGCTTTTCAA TTCAATTCAT CATTTTTTT TTATTCTTTT TTTTGATTTC   240
 241   GGTTTCTTTG AAATTTTTT GATTCGGTAA TCTCCGAACA GAAGGAAGAA CGAAGGAAGG   300
 301   AGCACAGACT TAGATTGTA TATATACGCA TATGTAGTGT TGAAGAAACA TGAAATTGCC   360
 361   CAGTATTCTT AACCCAACTG CACAGAACAA AAACCTGCAG GAAACGAAGA TAAATCATGT   420
 421   CGAAAGCTAC ATATAAGGAA CGTGCTGCTA CTCATCCTAG TCCTGTTGCT GCCAAGCTAT   480
 481   TTAATATCAT GCACGAAAAG CAAACAAACT TGTGTGCTTC ATTGGATGTT CGTACCACCA   540
 541   AGGAATTACT GGAGTTAGTT GAAGCATTAG GTCCCAAAAT TTGTTTACTA AAAACACATG   600
 601   TGGATATCTT GACTGATTTT TCCATGGAGG GCACAGTTAA GCCGCTAAAG GCATTATCCG   660
 661   CCAAGTACAA TTTTTACTC TTCGAAGACA GAAATTTGC TGACATTGGT AATACAGTCA    720
 721   AATTGCAGTA CTCTGCGGGT GTATACAGAA TAGCAGAATG GGCAGACATT ACGAATGCAC   780
 781   ACGGTGTGGT GGGCCCAGT ATTGTTAGCG GTTGAAGCA GCCGGCAGAA GAAGTAACAA    840
 841   AGGAACCTAG AGGCCTTTTG ATGTTAGCAG AATTGTCATG CAAGGGCTCC CTATCTACTG   900
 901   GAGAATATAC TAAGGTACT GTGACATTG CGAAGAGCGA CAAAGATTTT GTTATCGGCT    960
 961   TTATTGCTCA AAGAGACATG GGTGGAAGAG ATGAAGGTTA CGATTGGTTG ATTATGACAC  1020
1021   CCGGTGTGGG TTTAGATGAC AAGGGAGACG CATTGGGTCA ACAGTATAGA ACCGTGGATG  1080
1081   ATGTGGCTCT TACAGAGATCT GACATTATTA TTGTTGGAAG AGGACTATTT GCAAAGGGAA  1140
1141   GGGATGCTAA GGTAGAGGGT GAACGTTACA GAAAGCAGG CTGGAAGCA TATTGAGAA    1200
1201   GATGCGGCCA GCAAAACTAA AAAACTGTAT TATAAGTAAA TGCATGTATA CTAAACTCAC  1260
1261   AAATTAGAGC TTCAATTAA TTATATCAGT TATTACCCTA TGCGGTGTGA AATACCGCAC   1320
1321   AGATGCGTAA GGAGAAAATA CCGCATCAGG AAATTGTAAA CGTTAATATT TTGTTAAAT   1380
1381   TCGCGTTAAA TTTTTGTTAA ATCAGCTCAT TTTTTAACCA ATAGCCGAA ATCGGCAAAA   1440
1441   TCCCTATAAA ATCAAAAGAA TAGACCGAGA TAGGGTTGAG TGTTGTTCCA GTTGGAACA   1500
1501   AGAGTCCACT ATTAAAGAAC GTGACTCCA ACGTCAAAGG GCGAAAAACC GTCTATCAGG   1560
1561   GCGATGGCCC ACTACGTGAA CCATCACCCT AATCAAGTTT TTTGGGGTCG AGTGCCGTA   1620
1621   AAGCACTAAA TCGGAACCCT AAAGGGAGCC CCCGATTTAG AGCTTGACGG GGAAAGCCGG   1680
1681   CGAACGTGGC GAGAAAGGAA GGGAAGAAAG CGAAAGGAGC GGGCGCTAGG GCGCTGCAA   1740
1741   GTGTAGCCGGT CACGCTGCGC GTAACCACCA CACCCGCCGC GCTTAATGCG CCGCTACAGG  1800
```

FIG. 8B

```
1801 GCGGTCGCG CCATTCGCCA TTCAGGCTGC GCAACTGTTG GGAAGGGCGA TCGGTGCGGG 1860
1861 CCTCTTCGCT ATTACGCCAG CTGGCGAAAG GGGGATGTGC TGCAAGCCGA TTAAGTTGGG 1920
1921 TAACGCCAGG GTTTTCCCAG TCACGACGTT GTAAAACGAC GGCCAGTGAA TTGTAATACG 1980
1981 ACTCACTATA GGGCGAATTG GAGCTCGAAC ATGTTCACCG CGGTGCCGGC CGCTCTAGAA 2040
2041 CTAGTGGATC CCCCGGGCTG CAGGAATTCG ATATCAAGCT TATCGATACC GTCGACCTCG 2100
2101 AGAACATGTT CGGTACCAGC TTTTGTTCCC TTTAGTGAGG GTTAATTCCG AGCTTGGCGT 2160
2161 AATCATGGTC ATAGCTGTTT CCTGTGTGAA ATTGTTATCC GCTCACAATT CCACACAACA 2220
2221 TACGAGCCGG AAGCATAAAG TGTAAAGCCT GGGGTGCCTA ATGAGTGAGG TAACTCACAT 2280
2281 TAATTGCGTT GCGCTCACTG CCCGCTTTCC AGTCGGGAAA CCTGTCGTGC CAGCTGCATT 2340
2341 AATGAATCGG CCAACGCGCG GGGAGAGGCG GTTTGCGTAT TGGGCGCTCT TCCGCTTCCT 2400
2401 CGCTCACTGA CTCGCTGCGC TCGGTCGTTC GGCTGCGGCG AGCGGTATCA GCTCACTCAA 2460
2461 AGGCGGTAAT ACGGTTATCC ACAGAATCAG GGGATAACGC AGGAAAGAAC ATGTGAGCAA 2520
2521 AAGGCCAGCA AAAGGCCAGG AACCGTAAAA AGGCCGCGTT GCTGGCGTTT TTCCATAGGC 2580
2581 TCCGCCCCCC TGACGAGCAT CACAAAAATC GACGCTCAAG TCAGAGGTGG CGAAACCCGA 2640
2641 CAGGACTATA AAGATACCAG GCGTTTCCCC CTGGAAGCTC CCTCGTGCGC TCTCCTGTTC 2700
2701 CGACCCTGCC GCTTACCGGA TACCTGTCCG CCTTTCTCCC TTCGGGAAGC GTGGCGCTTT 2760
2761 CTCATAGCTC ACGCTGTAGG TATCTCAGTT CGGTGTAGT CGTTCGCTCC AAGCTGGGCT 2820
2821 GTGTGCACGA ACCCCCCGTT CAGCCCGACC GCTGCCGCCT ATCCGGTAAC TATCGTCTTG 2880
2881 AGTCCAACCC GGTAAGACAC GACTTATCGC CACTGGCAGC AGCCACTGGT AACAGGATTA 2940
2941 GCAGAGCGAG GTATGTAGGC GGTGCTACAG AGTTCTTGAA GTGGTGGCCT AACTACGGCT 3000
3001 ACACTAGAAG GACAGTATTT GGTATCTGCG CTCTGCTGAA GCCAGTTACC TTCGGAAAAA 3060
3061 GAGTTGGTAG CTCTTGATCC GGCAAACAAA CCACCGCTGG TAGCGGTGGT TTTTTTGTTT 3120
3121 GCAAGCAGCA GATTACGCGC AGAAAAAAAG GATCTCAAGA AGATCCTTTG ATCTTTTCTA 3180
3181 CGGGGTCTGA CGCTCAGTGG AACGAAAACT CACGTTAAGG GATTTTGGTC ATGAGATTAT 3240
3241 CAAAAAGGAT CTTCACCTAG ATCCTTTTAA ATTAAAAATG AAGTTTTAAA TCAATCTAAA 3300
3301 GTATATATGA GTAAACTTGG TCTGACAGTT ACCAATGCTT AATCAGTGAG GCACCTATCT 3360
3361 CAGCGATCTG TCTATTTCGT TCATCCATAG TTGCCTGACT CCCCGTCGTG TAGATAACTA 3420
3421 CGATACGGGA GGGCTTACCA TCTGGCCCCA GTGCTGCAAT GATACCGCGA GATCCACGCT 3480
3481 TTATCAGGGT TATTGTCTCA TGAGCGGATA CATATTTGAA TGTATTTAGA AAAATAAACA 3540
3541 AATAGGGGTT CCGCGCACAT TTCCCCGAAA AGTGCCACCT GGGTCCTTTT CATCACGTGC 3600
3601 TATAAAAATA ATTATAATTT AAATTTTTTA ATATAAATAT ATAAATTAAA AATAGAAAGT 3660
```

FIG. 8C

```
                1          2          3          4          5          6
       ---------|---------|---------|---------|---------|---------|
3661  AAAAAAAGAA ATTAAGAAAA AAATAGTTTT TGTTTTCCGA AGATGTAAAA GACTCTAGGG 3720
3721  GGATCGCCAA CAAATACTAC CTTTTATCTT GCTCTTCCTG CTCTCAGGTA TTAATGCCGA 3780
3781  ATTGTTTCAT CTTGTCTGTG TAGAAGACCA CACACGAAAA TCCTGTGATT TTACATTTTA 3840
3841  CTTATCGTTA ATCGAATGTA TATCTATTTA ATCGCTTTT CTTGTCTAAT AAATATATAT 3900
3901  GTAAAGTACG CTTTTGTTG AAATTTTTA AACCTTTGTT TATTTTTTT TCTTCATTCC 3960
3961  GTAACTCTTC TACCTTCTTT ATTACTTTC TAAAATCCAA ATACAAAACA TAAAAATAAA 4020
4021  TAAACACAGA GTAAATTCCC AAATTATTCC ATCATTAAAA GATACGAGGC GCGTGTAAGT 4080
4081  TACAGGCAAG CGATCCGTCC TAAGAAACCA TTATTATCAT GACATTAACC TATAAAAATA 4140
4141  GGCGTATCAC GAGGCCCTTT CGTC                                       4164
```

FIG. 9A

```
           10         20         30         40         50         60
   1 TCGCGCGTTT CGGTGATGAC GGTGAAAACC TCTGACACAT GCAGCTCCCG GAGACGGTCA   60
  61 CAGCTTGTCT GTAAGCGGAT GCCGGGAGCA GACAAGCCCG TCAGGGGCCG TCAGCGGGTG  120
 121 TTGGCGGGTG TCGGGGCTGG CTTAACTATG CGGCATCAGA GCAGATTGTA CTGAGAGTGC  180
 181 ACCATACCAC AGCTTTTCAA TTCAATTCAT CATTTTTTTT TTATTCTTTT TTTGATTTC   240
 241 GGTTCTTTG AAATTTTTTT GATTCGGTAA TCTCCGAACA GAAGGAAGAA CGAAGGAAGG  300
 301 AGCACAGACT TAGATTGGTA TATATACGCA TATGTAGTGT TGAAGAAACA TGAAATTGCC  360
 361 CAGTATTCTT AACCCAACTG CACAGAACAA AAACCTGCAG GAAACGAAGA TAAATCATGT  420
 421 CGAAAGCTAC ATATAAGGAA CGTGCTGCTA CTCATCCTAG TCCTGTTGCT GCCAAGCTAT  480
 481 TTAATATCAT GCACGAAAAG CAAACAAACT TGTGTGCTTC ATTGGATGTT CGTACCACCA  540
 541 AGGAATTACT GGAGTTAGTT GAAGCATTAG GTCCCAAAAT TTGTTTACTA AAAACACATG  600
 601 TGGATATCTT GACTGATTTT TCCATGGAGG GCACAGTTAA GCCGCTAAAG GCATTATCCG  660
 661 CCAAGTACAA TTTTTTACTC TTCGAAGACA GAAAATTTGC TGACATTGGT AATACAGTCA  720
 721 AATTGCAGTA CTCTGCGGGT GTATACAGAA TAGCAGAATG GCACAGACAT ACGAATGCAC  780
 781 ACGGTGTGGT GGGCCCAGTG ATTGTTAGCG GTTGAAGCA GCCGGCAGAA GAAGTAACAA  840
 841 AGGAACCTAG AGGCCTTTTG ATGTTAGCAG CAAGGCTCC CTATCTACTG GTTATCGGCT  900
 901 GAGAATATAC TAAGGGTACT GTTGACATTG CGAAGAGCGA CAAAGATTTT GTTATCGGCT  960
 961 TTATTGCTCA AAGAGACATG GGTGGAAGAG CGATTGGTTG ATTATGACAC ACCGTGGATG 1020
1021 CCGGTGTGGG TTTAGATGAC AAGGGAGACG CATTGGGTCA ACAGTATAGA ACCGTGGATG 1080
1081 ATGTGGTCTC TACAGGATCT GACATTATTA TTGTTGGAAG AGACTATTT GCAAAGGGAA 1140
1141 GGGATGCTAA GGTAGAGGGT GAACGTTACA GAAAAGCAGG CTGGAAGCA TATTTGAGAA 1200
1201 GATCGGCCA GCAAAACTAA AAAACTGTAT TGCATGTAAA TGCATGTGTA CTAAACTCAC 1260
1261 AAATTAGAGC TTCAATTTAA TTATATCAGT TATTACCCTA TGCCGTGTGA AATACCGCAC 1320
1321 AGATGCGTAA GGAGAAAATA CCGCATCAGG AAATTGTAAA CGTTAATATT TTGTTAAAAT 1380
1381 TCGCGTTAAA TTTTTGTTAA ATCAGCTCAT TTTTTAACCA ATAGGCCGAA ATCGGCAAAA 1440
1441 TCCCTTATAA ATCAAAAGAA TAGACCGAGA TAGGGTTGAG TGTTGTTCCA GTTTGGAACA 1500
1501 AGAGTCCACT ATTAAAGAAC GTGGACTCCA ACGTCAAAGG GCGAAAAACC GTCTATCGGT 1560
1561 GCGATGCCCC ACTACGTGAA CCATCACCCT TTTCAAGTTT TTTGGGGTCG AGTGCCGTA  1620
1621 AAGCACTAAA TCGGAACCCT AAAGGGAGCC CCGATTTAG AGCTTGACGG GGGCCTAGG  1680
1681 CGAACGTGGC GAGAAAGGAA GGGAAGAAAG CGAAAGGAGC GGGCGCTAGG GCGCTGGCAA  1740
1741 GTGTAGCGGT CACGCTGCGC GTAACCACCA CACCCGCCGC GCTTAATGCG CCGCTACAGG 1800
```

FIG. 9B

```
1801 GCGGTCGCG CCATTCGCCA TTCAGGCTGC GCAACTGTTG GGAAGGGCGA TCGGTGCGGG 1860
1861 CCTCTTCGCT ATTACGCCAG CTGGCGAAAG GGGGATGTGC TGCAAGGCGA TTAAGTTGGG 1920
1921 TAACGCCAGG GTTTTCCCAG TCACGACGTT GTAAAACGAC GGCCAGTGAA TTGTAATACG 1980
1981 ACTCACTATA GGGCGAATTG GAGCTCGAAC ATGTTCACCG CGGTGGCGC CGCTCTAGAA 2040
2041 CTAGTGGATC CTGCAAGCAG GATAGACGGC ATGCACGATT TGTAATAACA GAGTGTCTTG 2100
2101 TATTTTTAAA GAAAGTCTAT TTAATACAAG TGATTATATT AATTAACGT AAGCATCAGC 2160
2161 GGGTGACAAA ACGAGCATGC TTACTAATAA AATGTTAACC TCTGAGGAAG AATTGTGAAA 2220
2221 CTATCACTAA TGGTAGCTAT ATCGAAGAAT GGAGTTATCG GAATGGCCC TGATATTCCA 2280
2281 TGGAGTGCCA AAGGTGAACA GCTCCTGTTT AAAGCTATTA CCTATAACCA ATGGCTGTTG 2340
2341 GTTGGACGCA AGACTTTTGA ATCAATGGGA GCATTACCCA ACCGAAAGTA TGCGGTCGTA 2400
2401 ACACGTTCAA GTTTTACATC TGACAATGAG AACGTATTGA TCTTTCCATC AATTAAAGAT 2460
2461 GCTTTAACCA ACCTAAAGAA AATAACGGAT CATGTCATTG TTTCAGGTGG TGGGAGATA 2520
2521 TACAAAAGCC TGATCGATCA AGTAGATACA CTACATATAT CTACAATAGA CATCGAGCCG 2580
2581 GAAGGTGATG TTTACTTTCC TGAAATCCCC AGCAATTTTA GGCCAGTTTT TACCCAAGAC 2640
2641 TTCGCCTCTA ACATAAATTA TAGTTACCAA ATCTGGCAAA AGGGTTAACA AGTGGCAGCA 2700
2701 ACGGATTCGC AAACCTGTCA CGCCTTTTGT GCCAAAAGCC GGGCCAGGTT TGCGATCCGC 2760
2761 TGTGCCAGGC GTTAGGCGTC ATATGAAGAT TTCGGTGATC CCTGAGCAGG TGGCGGAAAC 2820
2821 ATTGGATGCT GAGAATTCGA TATCAAGCTT ATCGATACCG TCGACCTCGA GAACATGTTC 2880
2881 GGTACCAGCT TTTGTTCCCT TTAGTGAGGG TTAATTCCGA GCTTGGCGTA ATCATGGTCA 2940
2941 TAGCTGTTTC CTGTGTGAAA TTGTTATCCG CTCACAATTC CACACAACAT ACGAGCCGGA 3000
3001 AGCATAAAGT GTAAAGCCTG GGGTGCCTAA TGAGTGAGCT AACTCACATT AATTGCGTTG 3060
3061 CGCTCACTGC CCGCTTTCCA GTCGGGAAAC CTGTCGTGCC AGCTGCATTA ATGAATCGGC 3120
3121 CAACGCGCGG GGAGAGGCGG TTTGCGTATT GGGCGCTCTT CCGCTTCCTC GCTCACTGAC 3180
3181 TCGCTGCGCT CGGTCGTTCG GCTGCGGCGA GCGGTATCAG CTCACTCAAA GGCGGTAATA 3240
3241 CGGTTATCCA CAGAATCAGG GGATAACGCA GGAAAGAACA TGTGAGCAAA AGGCCAGCAA 3300
3301 AAGGCCAGGA ACCGTAAAAA GGCCGCGTTG CTGGCGTTTT TCCATAGGCT CCGCCCCCCT 3360
3361 GACGAGCATC ACAAAAATCG ACGCTCAAGT CAGAGGTGGC GAAACCCGAC AGGACTATAA 3420
3421 AGATACCAGG CGTTTCCCCC TGGAAGCTCC CTCGTGCGCT CTCCTGTTCC GACCCTGCCG 3480
3481 CTTACCGGAT ACCTGTCCGC CTTTCTCCCT TCGGGAAGCG TGGCGCTTTC TCATAGCTCA 3540
3541 CGCTGTAGGT ATCTCAGTTC GGTGTAGTC GTTCGCTCCA AGCTGGGCTG TGTGCACGAA 3600
```

FIG. 9C

```
3601  CCCCCGTTC  AGCCCGACCG  CTGGCCTTA  TCCGGTAACT  ATCGTCTTGA  GTCCAACCCG  3660
3661  GTAAGACACG  ACTTATCGCC  ACTGGCAGCA  GCCACTGGTA  ACAGGATTAG  CAGAGCGAGG  3720
3721  TATGTAGGCG  GTGCTACAGA  GTTCTTGAAG  TGGTGCCTA   ACTACGGCTA  CACTAGAAGG  3780
3781  ACAGTATTTG  GTATCTCGCC  TCTGCTGAAG  CCAGTTACCT  TCGGAAAAAG  AGTTGGTAGC  3840
3841  TCTTGATCCG  GCAAACAAAC  CACCGCTGGT  AGCGGTGGTT  TTTTTGTTTG  CAAGCAGCAG  3900
3901  ATTACGCGCA  GAAAAAAAGG  ATCTCAAGAA  GATCCTTTGA  TCTTTTCTAC  GGGGTCTGAC  3960
3961  GCTCAGTGGA  ACGAAAACTC  ACGTTAAGGG  ATTTTGGTCA  TGAGATTATC  AAAAAGGATC  4020
4021  TTCACCTAGA  TCCTTTTAAA  TTAAAAATGA  AGTTTTAAAT  CAATCTAAAG  TATATATGAG  4080
4081  TAAACTTGGT  CTGACAGTTA  CCAATGCTTA  ATCAGTGAGG  CACCTATCTC  AGCGATCTGT  4140
4141  CTATTTCGTT  CATCCATAGT  TGCCTGACTC  CCCGTCGTGT  AGATAACTAC  GATACGGGAG  4200
4201  GGCTTACCAT  CTGGCCCCAG  TGCTGCAATG  ATACCGATTA  TTGAAGCATT  TATCAGGGTT  4260
4261  ATTGTCTCAT  GAGCGGATAC  ATATTTGAAT  GTATTTAGAA  AAATAAACAA  ATAGGGGTTC  4320
4321  CGCGCACATT  TCCCCGAAAA  GTGCCACCTG  GGTCCTTTTC  ATCACGTGCT  ATAAAAATAA  4380
4381  TTATAATTA   AATTTTTTAA  TATAAATATA  TAAATTAAAA  ATAGAAAGTA  AAAAAAGAAA  4440
4441  TTAAAGAAAA  AATAGTTTTT  GTTTTCCGAA  GATGTAAAAG  ACTCTAGGGG  GATCGCCAAC  4500
4501  AAATACTACC  TTTTATCTTG  CTCTTCCTGC  TCTCAGGTAT  TAATGCCGAA  TTGTTTCATC  4560
4561  TTGTCTGTGT  AGAAGACCAC  ACACGAAAAT  CCTGTGATTT  TACATTTAC   TTATCGTTAA  4620
4621  TCGAATGTAT  ATCTATTAA   TCTGCTTTTC  TTGTCTAATA  AATATATATG  TAAAGTACGC  4680
4681  TTTTTGTTGA  AATTTTTAA   ACCTTTGTT   ATTTTTTTT   CTTCATTCCG  TAACTCTTCT  4740
4741  ACCTTCTTTA  TTTACTTTCT  AAAATCCAAA  TACAAAACAT  AAAAATAAAT  AACACAGAG   4800
4801  TAAATTCCCA  AATTATTCCA  TCATTAAAAG  ATACGAGCG   CGTGTAAGTT  ACAGGCAAGC  4860
4861  GATCCGTCCT  AAGAAACCAT  TATTATCATG  ACATTAACCT  ATAAAAATAG  GCGTATCACG  4920
4921  AGGCCCTTTC  GTC                                                          4933
        |          |          |          |          |          |
        10         20         30         40         50         60
```

FIG. 10

```
         10         20         30         40         50         60
         |          |          |          |          |          |
  1 TGTTCACCGC GGTGGCGGCC GCTCTAGAAC TAGTGGATCC TGCAAGCAGG ATAGACGGCA  60
 61 TGCACGATTT GTAATAACAG AGTGTCTTGT ATTTTTAAAG AAAGTCTATT TAATACAAGT 120
121 GATTATATTA ATTAACGGTA AGCATCAGCG GGTGACAAAA CGAGCATGCT TACTAATAAA 180
181 ATGTTAACCT CTGAGAAGA AGCATCAGCG GGTGACAAAA CGAGCATGCT TACTAATAAA 180
181 ATGTTAACCT CTGAGAAGA ATTGTGAAAC TATCACTAAT GGTAGCTATA TCGAAGAATG 240
241 GAGTTATCGG GAATGGCCCT GATATTCCAT GGAGTGCCAA AGTGAACAG CTCCTGTTTA 300
301 AAGCTATTAC CTATAACCAA TGGCTGTTGG TTGGACGCAA GACTTTTGAA TCAATGGGAG 360
361 CATTACCCAA CCGAAAGTAT GCGGTCGTAA CACGTTCAAG TTTTACATCT GACAATGAGA 420
421 ACGTATTGAT CTTTCCATCA ATTAAAGATG CTTAACCAA CCTAAAGAAA ATAACGATC 480
481 ATGTCATTGT TTCAGTGTGT GGGAGATAT ACAAAAGCCT GATCGATCAA GTAGATACAC 540
541 TACATATATC TACAATAGAC ATCGAGCCGG AAGGTGATGT TTACTTTCCT GAAATCCCCA 600
601 GCAATTTAG GCCAGTTTTT ACCCAAGACT TCGCCTCTAA CATAAATTAT AGTTACCAAA 660
661 TCTGGCAAAA GGGTTAACAA GTGCCAGCAA CGGATTCGCA AACCTGTCAC GCCTTTGTG 720
721 CCAAAAGCCG CGCCAGGTTT GCCGATCCGCT GTGCCAGGCG TTAGGCGTCA TATGAAGATT 780
781 TCGGTGATCC CTGAGCAGT GCGGAAACA GGCGAAACA TTGGATGCTG AGAATTCGAT ATCAAGCTTA 840
841 TCGATACCGT CGACCTCGAG AACA                                          864
         |          |          |          |          |          |
         10         20         30         40         50         60
```

IN VITRO TRANSPOSITION OF ARTICLE TRANSPOSONS

This application is a division of application Ser. No. 08/204,675, filed Mar. 2, 1994, now U.S. Pat. No. 5,677,170.

The U.S. Government has a paid-up license in this invention and the right in limited circumstances to require the patent owner to license others on reasonable terms as provided for by the terms of grant number GM36481 and NSF RCD9154644.

BACKGROUND OF THE INVENTION

DNA sequencing has helped revolutionize the way that genes and genomes are studied, and has led to a greater understanding of most aspects of biology. Nevertheless, with efforts underway to map and sequence the genomes of a variety of organisms, the need to improve the efficiency of DNA sequencing has never been greater (1). One of the major problems associated with sequencing large segments of DNA is obtaining sequence information beyond the limits of a single primer extension event. Several techniques are currently used to acquire sequences within the interior of a DNA insert; these include: i) the synthesis of custom primers to "walk" along a segment of DNA (2, 3), ii) shotgun subcloning, which requires a high degree of redundancy for complete sequence recovery (4), or iii) the construction of overlapping exonuclease deletion clones (3, 5). Each of these methods is time-consuming, idiosyncratic and therefore difficult to automate, and/or costly.

Alternatively, transposable elements have been adapted for DNA mapping and sequencing. Examples include: γδ (6), Tn5 (7), Tn10 (8), as well as derivatives of these and other transposons. Although these approaches generally offer great promise, the insertion step is performed in vivo in *E. coli*; hence, transposition may occur into either the plasmid target or the *E. coli* genome, complicating the recovery of target insertions. An additional difficulty arises from host effects on insertion randomness, i.e., "hotspots" and "coldspots" of integration are often observed in vivo (9).

The complete DNA integration reaction employed by certain retroviruses and retrotransposons as part of their normal life cycles can be carried out completely in vitro (10–14) offering a possible alternative to in vivo transposon insertion techniques for DNA sequencing.

There is a need in the art for a simple, reliable technique for generating sets of DNA templates for sequencing any target. In particular there is a need for sets of DNA templates which are amenable to automated sequencing with a single set of primers.

SUMMARY OF THE INVENTION

It is an object of the invention to provide methods for providing templates for DNA sequencing.

It is another object of the invention to provide methods for sequencing such DNA templates.

It is yet another object of the invention to provide a kit for DNA sequencing.

It is yet another object of the invention to provide an artificial transposon.

It is still another object of the invention to provide plasmids for preparing artificial transposons.

It is yet another object of the invention to provide methods for the generation in vitro of insertions into a target DNA molecule.

These and other objects of the invention are provided by one or more of the embodiments of the invention described below. In one embodiment a method is provided for preparing templates for DNA sequencing. The method comprises the steps of:

incubating in vitro (1) a population of a plasmid, said plasmid comprising a region of DNA to be sequenced, (2) yeast retrotransposon Ty1 integrase, and (3) an artificial transposon having two termini which are substrates for Ty1 integrase, wherein the molar ratio of artificial transposon to plasmid is at least 1:1, to form a population of plasmids with quasi-randomly integrated insertions of the artificial transposon;

transforming host cells with the population of plasmids with quasi-randomly integrated insertions of the artificial transposon;

selecting those host cells which have been transformed with a plasmid with an insertion of the artificial transposon;

isolating plasmid DNA from those host cells which have been transformed with a plasmid with an insertion of the artificial transposon, said plasmid DNA being suitable for use as a DNA sequencing template.

In another embodiment a method is provided for sequencing DNA. The method comprises the steps of:

incubating in vitro (1) a population of a plasmid, said plasmid comprising a region of DNA to be sequenced, (2) yeast retrotransposon Ty1 integrase, and (3) an artificial transposon having two termini which are substrates for Ty1 integrase, wherein the molar ratio of artificial transposon to plasmid is at least 1:1, to form a population of plasmids with quasi-randomly integrated insertions of the artificial transposon;

transforming host cells with the population of plasmids with quasi-randomly integrated insertions of the artificial transposon;

selecting those host cells which have been transformed with a plasmid with an insertion of the artificial transposon;

isolating plasmid DNA from those host cells which have been transformed with a plasmid with an insertion of the artificial transposon, said plasmid DNA being suitable for use as a DNA sequencing template;

hybridizing to said isolated plasmid DNA a primer which is complementary to a terminus of the artificial transposon;

extending said primer to determine a nucleotide sequence of plasmid DNA flanking said artificial transposon.

In still another embodiment of the invention a method for sequencing DNA is provided. The method comprises the steps of:

providing a population of plasmids with quasi-randomly integrated insertions of an artificial transposon, said artificial transposon having termini which are substrates for yeast retrotransposon Ty1, said population of plasmids having been formed by in vitro insertion of said artificial transposon into the plasmids using yeast retrotransposon Ty1 integrase and a molar ratio of artificial transposon to plasmid of at least 1:1;

hybridizing to individual plasmids of said population a primer which is complementary to a terminus of the artificial transposon;

extending said primer to determine a nucleotide sequence of plasmid DNA flanking said artificial transposon.

In still another embodiment of the invention a kit for DNA sequencing is provided. The kit comprises:

an artificial transposon having termini which are substrates for yeast retrotransposon Ty1 integrase;

yeast retrotransposon Ty1 integrase;
a buffer for in vitro transposition of said artificial transposon, said buffer having a pH of 6 to 8 and 1 to 50 mM $Mg^{+2}$; and
a primer which is complementary to a terminus of said artificial transposon.

In an additional embodiment of the invention an artificial transposon is provided. The transposon consists of a linear DNA molecule comprising:
a marker gene;
a sequence of yeast retrotransposon Ty1, said sequence selected from the group consisting of a U5 sequence and a U3 sequence, said sequence flanking said marker gene on its upstream end, said sequence consisting of 4 to 11 bp of terminal sequences of said Ty1; and
a sequence of yeast retrotransposon Ty1, said sequence selected from the group consisting of a U5 sequence and a U3 sequence, said sequence flanking said marker gene on its downstream end, said sequence consisting of 4 to 11 bp of terminal sequences of said Ty1.

In yet an additional embodiment of the invention a plasmid useful for generating artificial transposons is provided. The plasmid comprises:
an origin of replication;
a first selectable marker gene;
two blunt-ended transposon termini of at least 4 bp each, said termini being substrates for yeast retrotransposon Ty1 integrase, said transposon termini flanking a first restriction enzyme site useful for insertion of a second selectable marker gene to form an artificial transposon;
a second restriction enzyme site flanking said two transposon termini, wherein digestion with said second restriction enzyme liberates a blunt-ended fragment having said transposon termini at either end of the fragment, the fragment thereby liberated being an artificial transposon.

In still another embodiment of the invention a method for in vitro generation of insertions into a target plasmid is provided. The method comprises the steps of:
incubating in vitro (1) a population of a plasmid (2) yeast retrotransposon Ty1 integrase, and (3) an artificial transposon having termini which are substrates for Ty1 integrase, wherein the molar ratio of artificial transposon to plasmid is at least 1:1, to form a population of plasmid molecules with quasi-randomly integrated insertions of the artificial transposon;
transforming a host cell with the population of plasmid molecules with quasi-randomly integrated insertions of the artificial transposon;
selecting those host cells which have been transformed with a plasmid molecule with an insertion of the artificial transposon.

The in vitro systems of the present invention offer several advantages over in vivo transposition systems: i) special bacterial strains are not required, ii) potential host effects are avoided, and iii) an in vitro reaction is amenable to biochemical alteration and parameter optimization. Thus a simple and reliable method is provided for generating large amounts of sequence information, such as is required for sequencing of entire genomes of particular organisms.

BRIEF DESCRIPTION OF THE DRAWINGS

FIG. 1. Overview of Artificial Transposon Insertion into Plasmid Targets.

The basic steps involved in generating artificial transposon insertions in target plasmids are indicated. Note the following: DNA sequences to be determined (dashed line) trimethoprim resistance ($tri^r$) gene (shaded box); target plasmid (double circle); PART (primer island artificial transposon) (box); Ty1 U3 termini (filled rectangles).

FIG. 2. pAT-1 and pAT-2.

Figure 2A:
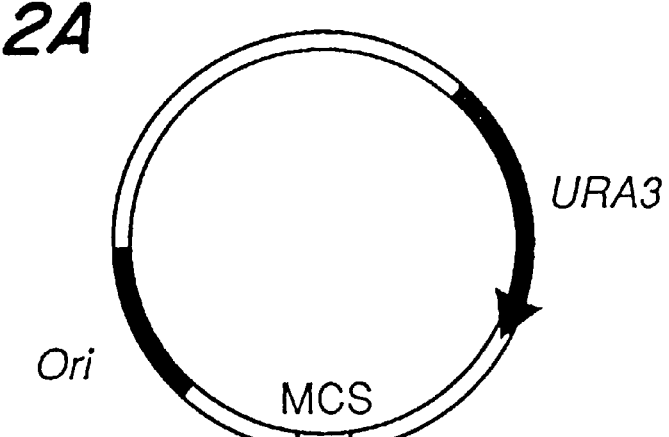
Figure 2B:
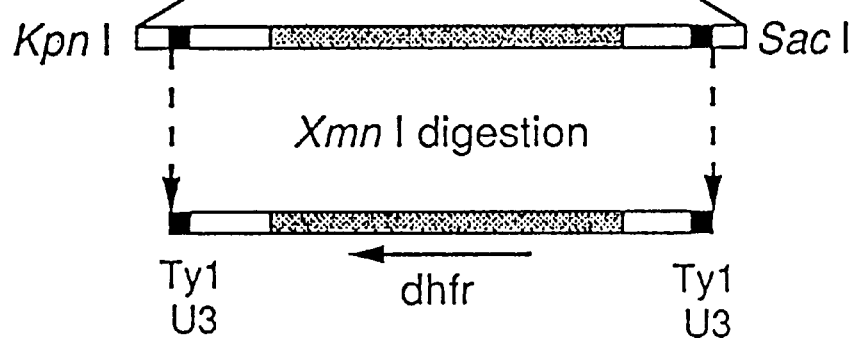
Figure 2C:
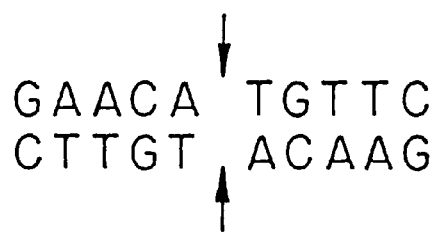

FIG. 2A. The backbone common to pAT-1 and pAT-2 is shown to contain the yeast URA3 gene, a bacterial origin of replication (ori) and a multicloning site (mcs). pAT-2, containing the PART insert, is depicted. FIG. 2B. The PART which is created upon digestion with Xmn I, is shown. It contains the dhfr (dihydrofolate reductase) gene (stippled), the pBLUESCRIPT mcs (white boxes), and Ty1 U3 cassettes (filled rectangles), as well as two unique primer sites for sequencing the DNA flanking an insertion site. FIG. 2C. The sequence at Ty1 U3/Xmn I cassettes. The arrows indicate the Xmn I cleavage site. The shaded areas indicate Ty1 U3 sequences (one on either side of the arrows), while the entire sequence encodes a recognition site for Xmn I.

Figure 3:
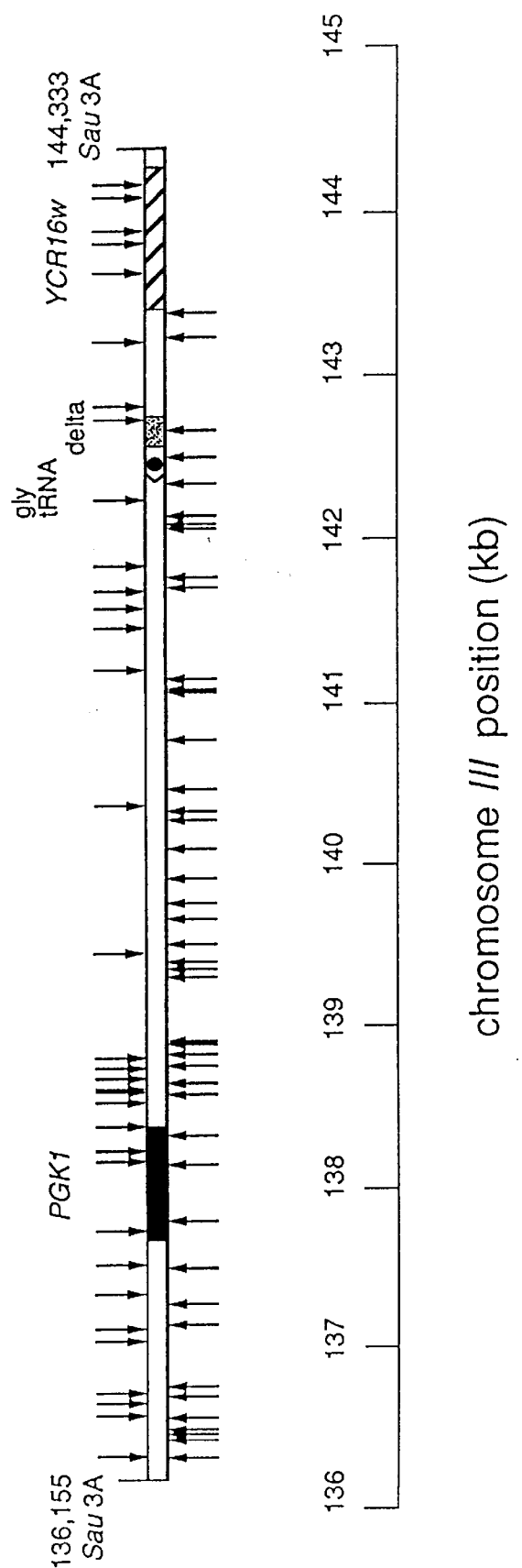

FIG. 3. PART Insertions in Clone p76-2.

The 8 kb insert of clone p76-2, containing a segment of yeast chromosome III, is shown along with the sites of 78 independent PART insertions (arrows). The orientation of transposon insertion is indicated: (↓) Forward (the dhfr gene in the artificial transposon is transcribed left to right, or (↑) Reverse. This region of chr. III contained on the insert includes the PGK 1 gene (black box), a glycine tRNA gene (black circle with arrowhead indicating direction of transcription), a Ty1 solo delta (stippled box) and the YCR16w locus (striped box). The PART insertion locations were determined by sequencing one or both insertion junctions.

Figure 4:
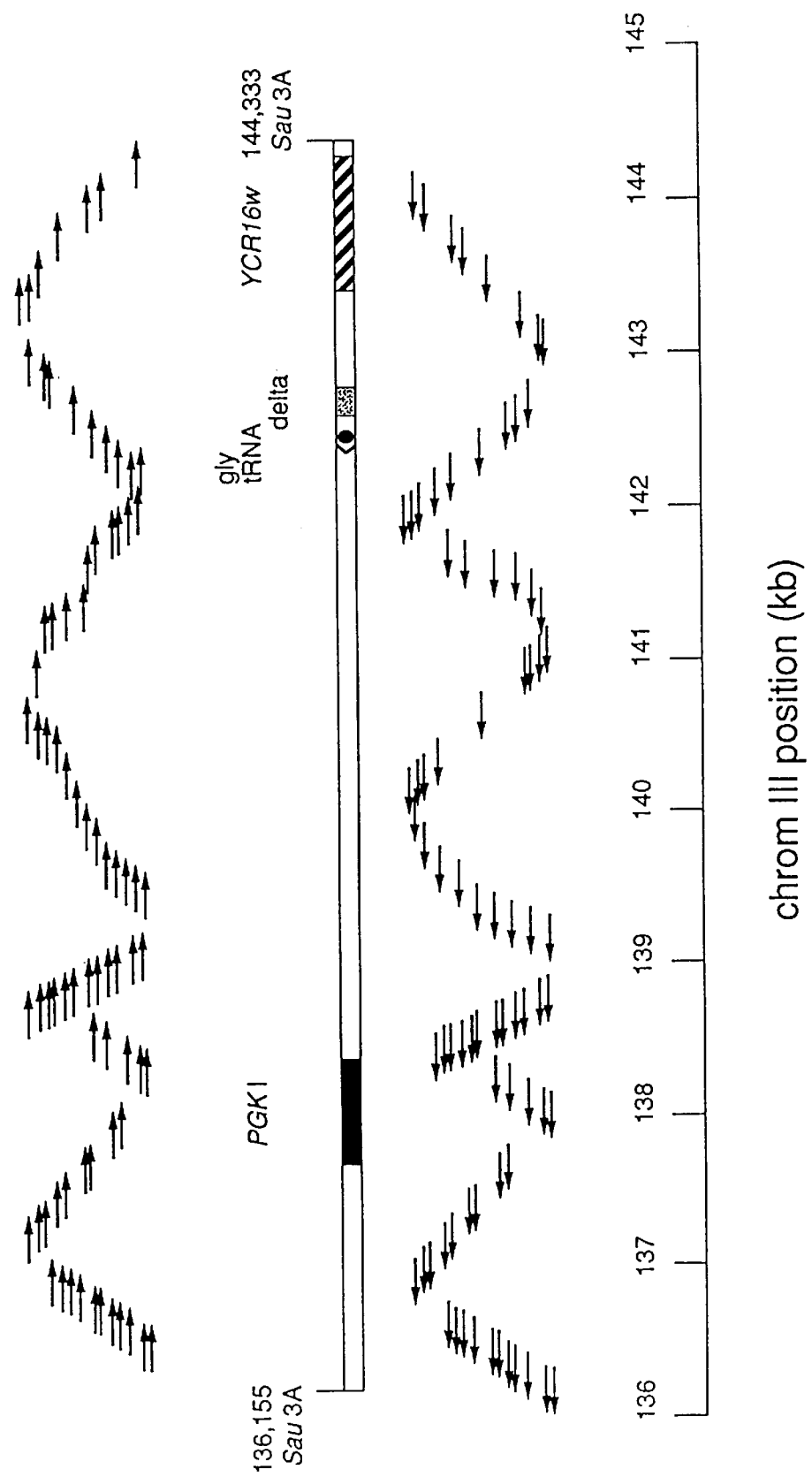

FIG. 4. Conceptual Contig Map.

The locations of the 78 PART insertions were used to construct a conceptual contig map based on the following assumptions: i) two primer extensions would be initiated from each PART (one in each direction) and ii) each extension would lead to the recovery of 250 bp of useful DNA sequence information.

Figure 5:
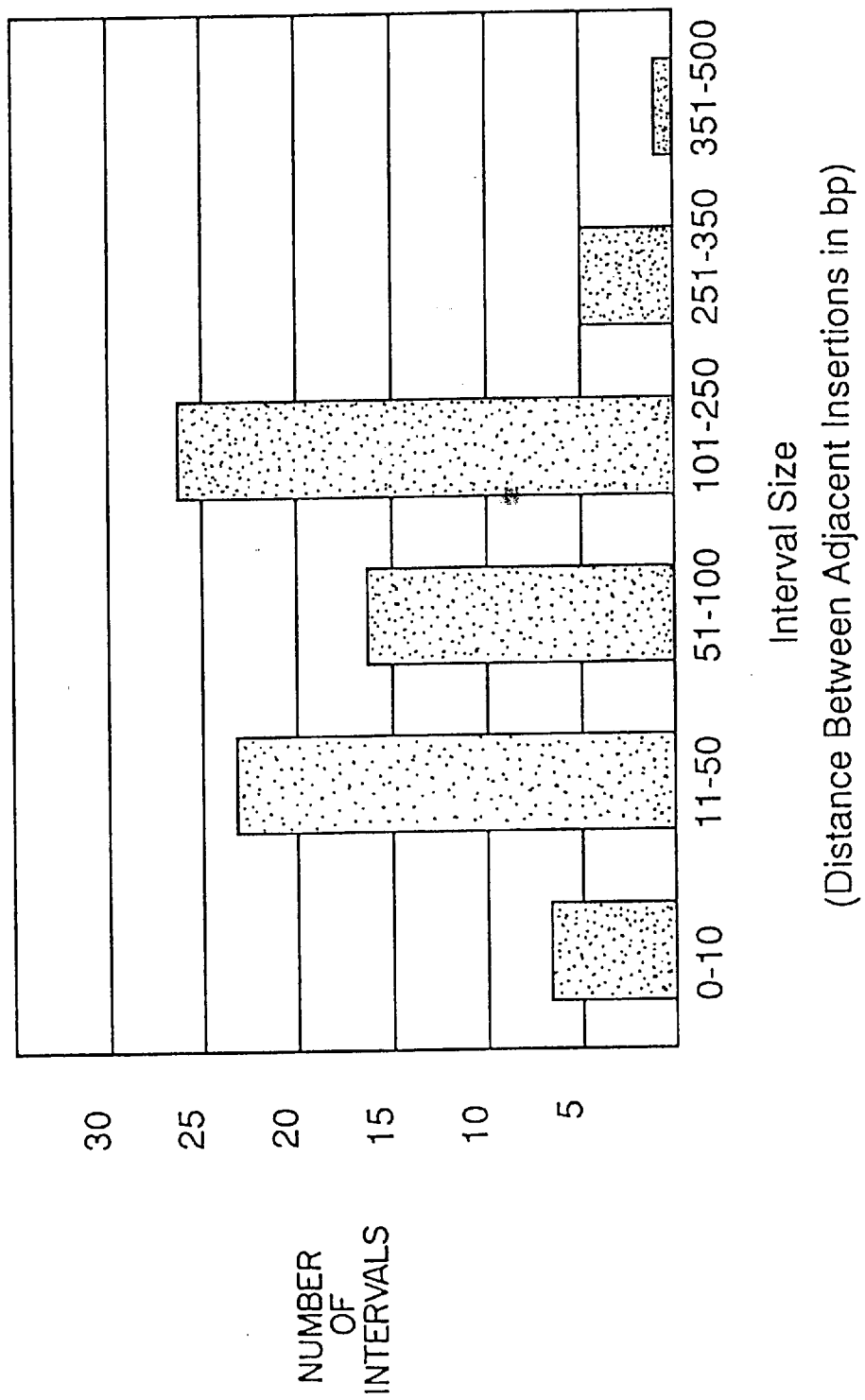

FIG. 5. Interval Sizes of PART Insertions into p76-2.

The size of intervals between individual insertions of PART into p76-2 (i.e., the distance between adjacent insertions in bp) were grouped and the number of intervals falling within each group is graphically represented.

Figure 6:
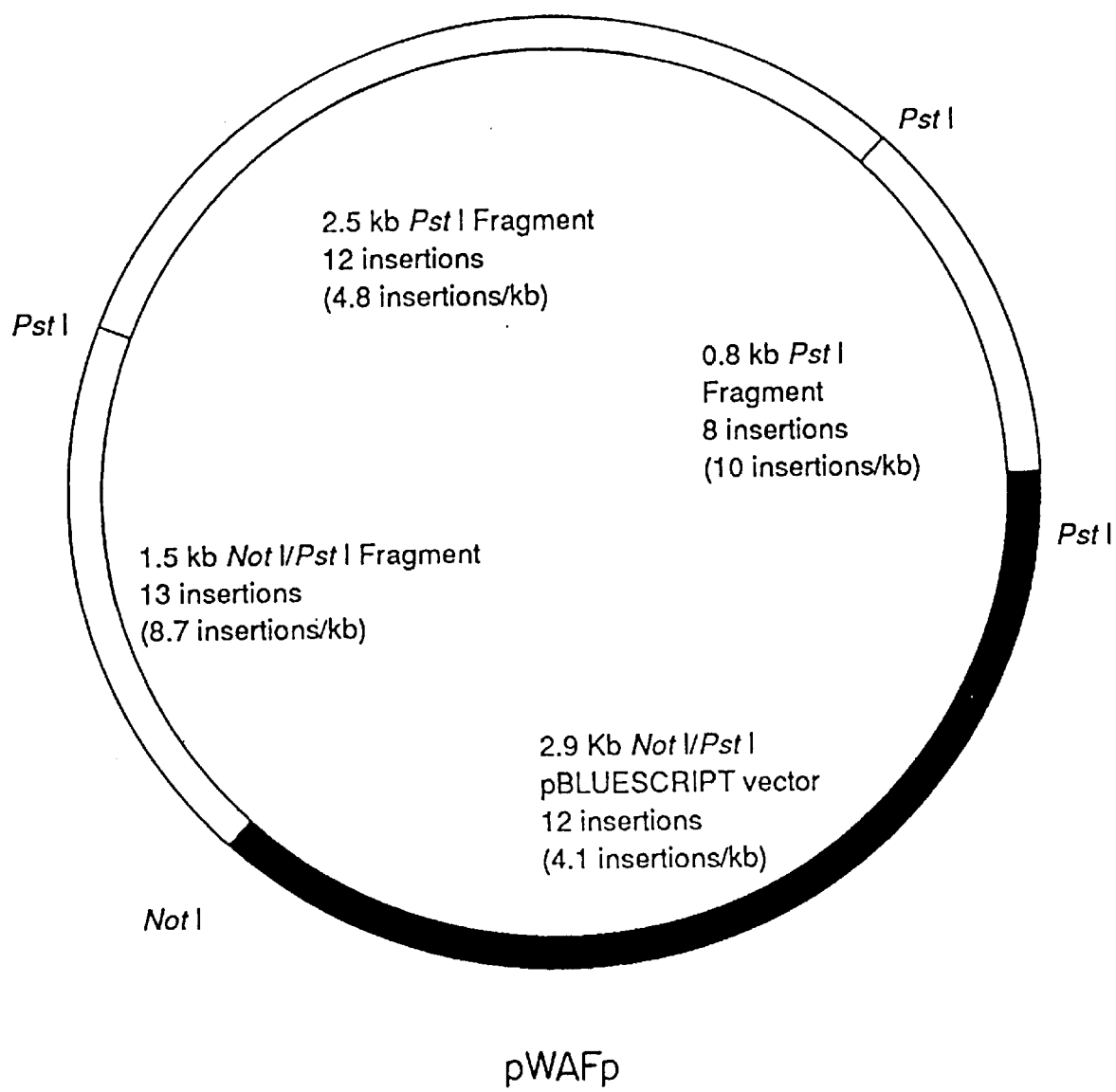

FIG. 6. Distribution of PART Insertions in Plasmid pWAFp.

Plasmid pWAFp contains a 5 kb insert of human DNA encoding the WAF-1 promoter. We generated PART insertions into this target using an artificial transposon prepared by PCR and digestion with Bbs I to generate U3 and U5 sequences at the upstream and downstream ends of the transposon, respectively. Of 45 insertions analyzed, 12 mapped to the pBLUESCRIPT vector fragment (shown in black), 13 mapped to the 1.5 kb Not I/Pst I fragment of WAF-1 insert, 12 mapped to the 2.5 kb Pst I fragment of WAF-1 (WAF-1 sequences are solid white). Hence, insertions were recovered from all regions of this target plasmid, and the insertion frequencies ranged from 4.1 insertions/kb to 10 insertions/kb target DNA. This set of insertions was then used to directly recover greater than 90% of the WAF-1 DNA sequence.

Figure 7:
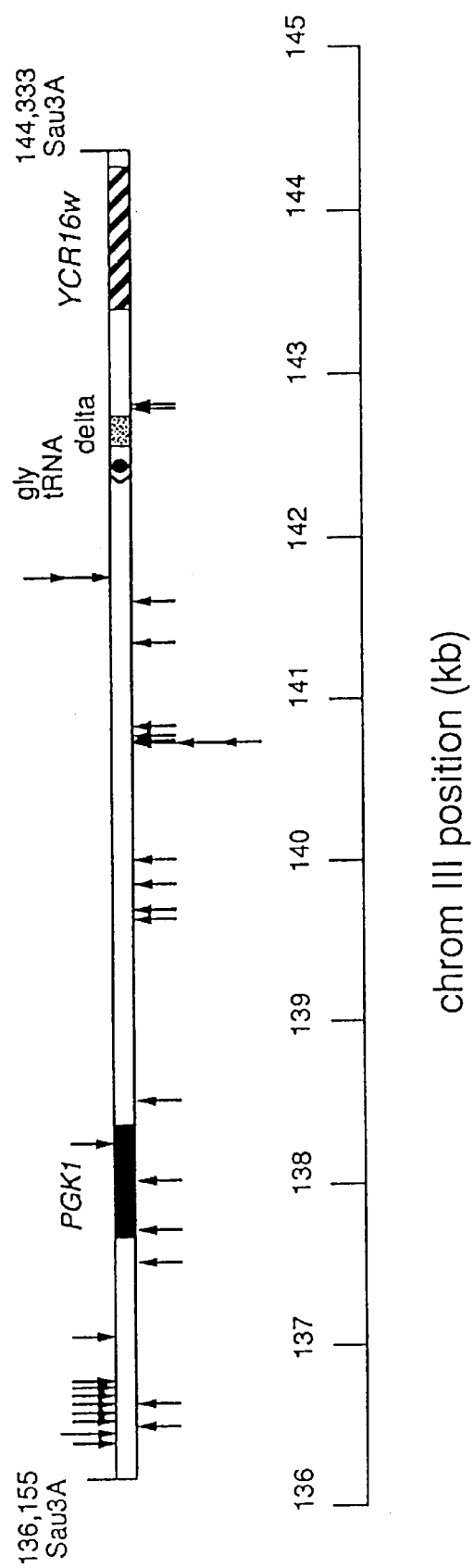

FIG. 7. Distribution of Insertions into Yeast Chromosome III.

An artificial transposon having one U3 and one U5 terminus, each 4 bp in length, was generated by PCR, digested with Bbs I, and filled-in with Klenow fragment of DNA polymerase I. Distribution of insertions are shown on a map of the chromosome III segment of DNA contained on the target plasmid.

FIGS. 8A, 8B, and 8C. The nucleotide sequence of pAT-1.

FIGS. 9A, 9B, and 9C. The nucleotide sequence of pAT-2.

FIG. 10. The nucleotide sequence of the PART from pAT-2.

DETAILED DESCRIPTION OF THE PREFERRED EMBODIMENTS

It is a discovery of the present invention that a transposon insertion technique that is carried out entirely in vitro may be applied to a variety of problems, including DNA sequencing. This technique employs artificial transposons which are created using a plasmid construct, and retroviral or retrotransposon integrase, which may be provided in the form of viral or virus-like particles (VLPs), which mediates the insertion of these transposons into target DNA molecules.

We have developed new methods for creating artificial transposons and efficiently inserting these transposons into plasmid targets, in vitro. There are three key aspects of the process: i) the in vitro integration reaction is highly efficient, giving rise to thousands of integrations per reaction; with most plasmid targets, this efficiency approaches one insertion per phosphodiester bond, ii) the insertion process is sufficiently random that transposon integrations occur throughout target plasmid sequences, and iii) virtually any DNA sequence or combination of sequences can, in principle, serve as an artificial transposon. These three features combine to make this an extremely versatile method of generating recombinant DNA molecules.

Artificial transposons are ideal for DNA sequencing: i) a large number of transposon insertions can be easily assembled from a single integration reaction, allowing the recovery of insertions suitably spaced to facilitate sequencing of a DNA segment, ii) the transposon can be engineered to contain desired features useful for DNA mapping or sequencing, and iii) since each transposon carries two unique primer sites, the nucleotide sequence flanking each insertion site can be rapidly and efficiently determined. A set of plasmids bearing artificial transposon insertions are especially useful for sequencing because all the plasmids can be sequenced in parallel using a defined pair of primers. This is in contrast to the inefficient "series" approach of primer walking, in which each sequence is used to specify the next primer. Hence, artificial transposons are flexible and extremely efficient for generating DNA sequencing templates useful for both small and large-scale DNA sequencing projects.

There are three macromolecular components to the in vitro integration reaction: i) an artificial transposon, ii) retroviral or retrotransposon integrase and iii) a DNA target. These three components are mixed together in a reaction containing the appropriate buffer and cofactors. In the case of yeast retrotransposon Ty1, the reaction is briefly incubated at 30° and 37° Celsius, and terminated by adding EDTA and heating to 65° Celsius. Finally, the nucleic acids are phenol/chloroform extracted and ethanol precipitated. The recovered DNA is used to transform a host cell to drug resistance (or other suitable selectable marker), allowing the identification of target molecules which have received a transposon integration (FIG. 1). A set of transposon-bearing target DNA molecules may then be used directly to obtain the DNA sequences flanking the insertion sites, using two primers corresponding to the transposon termini; a collection of such insertions can be used for the efficient recovery of DNA sequence information from the region of interest.

We have focused our initial efforts on developing a specific application of this technology, i.e., in vitro insertion of "primer island" artificial transposons (PARTs) into plasmid targets for the purpose of DNA mapping and sequencing. In addition to the features mentioned above (efficiency of integration, randomness of insertion, and flexibility of transposon), this system has other advantages compared with existing methods, including: i) the in vitro protocol is simple and highly reliable, even in the hands of a novice, ii) the PART does not contain large terminal repeats which, in Tn5 and Tn10-based systems, hinder access to sequences flanking the insertion junctions, and iii) the reaction is carried out completely in vitro and therefore is amenable to biochemical alteration and parameter optimization; this may be especially useful with unusual DNA templates such as those containing tandem sequence repeats, high GC content, or unusual template topology which might represent difficult targets.

Importantly, transposon integration within targets was sufficiently random that insertions were recovered from all regions of target plasmids. Hence, Ty1 integrase-mediated integration in vitro is, at a minimum, a nearly-random process. It may, in fact, be totally random. This will only become clear upon testing large numbers of targets containing different DNA sequence features. Nevertheless, our current results strongly support a model of quasi-random insertion with no apparent major biases. In contrast, this feature is not generally observed of other transposon systems adapted for DNA sequencing; instead, hotspots and coldspots of insertion frequently lead to a non-random distribution of insertions rendering these systems incapable of accessing large segments of DNA sequence, or high levels of wasteful redundancy in other regions. These problems have been circumvented in some systems with mutant transposases which display altered target specificity (9). However, this approach provides only a limited relaxation of transposase-specified target specificity. It is known that host cell factors contribute to target specificity in vivo for both Tn10 (9, 9a) and Ty1 (28); such target specificity is eliminated by the use of in vitro systems as taught herein. Fortunately, the process of artificial transposon integration in vitro by retroviral and retrotransposon integrases, such as Ty1 integrase, displays random-like behavior (FIG. 2), making it ideal for the purpose of DNA sequencing. Quasi-random, according to the present invention, means that insertions can be obtained in virtually any sequence at a spacing of at least one integration per kb. In practice, integrations have been obtained at maximum spacings of as low as one integration per 500 bp, or even one integration per 400 bp. In contrast, large cold-spots have been found in targets of Ty1 transposition in vivo.

Because our method of constructing artificial transposons is very versatile, transposons containing a variety of sequences can be constructed for a number of specific applications. For example, other markers can be inserted into the multicloning site (mcs) site of pAT-1, including but not limited to yeast and mammalian drug-selectable or auxotrophic genes, generating marker cassettes that can act as transposons. Such artificial transposons can be used for "marker addition", i.e., the insertion of a useful auxotrophic marker into an acceptable region of a plasmid of interest. For use in bacteria or yeast, for example, pAT-1 derivatives containing a variety of selectable markers in the mcs can be constructed, and the marker of choice (auxotrophic, drug resistance, suppressor, etc.) can be added to a target plasmid with a simple in vitro integration reaction. Indeed, the products of a single integration reaction can be viewed as an "integration library" containing a collection of insertions, each clone containing a single insertion at a particular phosphodiester bond. Should it be necessary, an insertion at any specific phosphodiester bond can be identified with conventional library screening methods, using a junction oligonucleotide as a probe. Hence, using a custom artificial transposon, and applying the appropriate screening method, recombinant molecules of a desired structure can be recovered.

In addition to the artificial transposon, the other two components of the system, i.e., the integrase and the target, are also versatile. For example, other integrases or transposases can effect an equivalent or nearly-equivalent in vitro integration reaction. In addition, mutant integrases are also useful. The specific properties of such integrases might together provide a wider range of integration preferences or frequencies. Also, rather than providing the integrase in the form of viral particles or VLPs, purified integrases can be used. These may display altered levels of activity or stability, relative to VLP-associated integrases.

The in vitro integration reaction can employ a variety of DNA targets. Plasmids, cosmids, artificial chromosomes, as well as bacteriophage or viral vectors are useful. Bacteriophage lambda DNA has been used as a target in similar reactions using Moloney murine leukemia virus (10) and Ty1 integrases (11, 12) provided in the form of viral particles.

The PART-based system for generating DNA sequencing templates can be readily applied to the development of high throughput, massively parallel DNA sequencing strategies. The high degree of randomness of insertion and the large fraction of clones generating useful sequence data mean that a shotgun approach to sequencing of large recombinant plasmids, including cosmids as well as P1 and bacterial artificial chromosomes, is feasible and highly suited to automation. Random doubly drug resistant colonies can be selected, their DNA extracted, and fed directly into an automated sequencing apparatus. All of these steps are amenable to automation. Because a single set of optimized primers can be used to sequence an entire set of plasmid derivatives, all of the steps can be done in parallel without operator intervention with regard to primer design and selection, etc. Hence, although artificial transposon-facilitated DNA sequencing is predicted to be very useful for small-scale sequencing projects, it may be even more useful for massive projects such as the effort underway to map and sequence the human genome.

The artificial transposon which is employed according to the present invention contains a 3'-hydroxyl and is blunt-ended. Such molecules can be prepared using restriction enzymes which make staggered cuts followed by a "filling-in" reaction with a DNA polymerase, such as Klenow fragment of DNA polymerase I. Alternatively, the artificial transposon can be prepared by a PCR. Typically the ends of PCR products require "trimming" to generate blunt ends. Thus a restriction enzyme, such as Xmn I, which makes blunt-ended termini can be used to trim a PCR product. Most simply, an artificial transposon contained in a plasmid can be isolated from the plasmid with a restriction enzyme, such as Xmn I, which makes blunt-ended termini. This provides a homogenous preparation of blunt-ended fragments in one step.

Integrase activity can be provided by virus-like particles, in the case of yeast retrotransposon Ty1, or by cellular nucleoprotein complexes in the case of retroviral particles. Alternatively, purified integrase may be used. It is desirable that the artificial transposon be added to the in vitro transposition incubation mixtures as protein-free DNA preparations. Although some native transposon DNA may be present in the integrase preparations, typically such transposons will not be genetically marked, and will be present in significantly lower molar amounts than the artificial transposon.

DNA contained within a transposon's termini may be any desirable marker or even cryptic sequence. Antibiotic resistance genes, useful for either prokaryotes or eukaryotes are often useful. Auxotrophic markers are also useful, especially in yeast. Cis-acting regulatory elements, such as promoters, may also be desired to ascertain function of previously unknown regions flanking an insertion.

The ratio of artificial transposon to target DNA has been found to be a significant factor in the efficiency of the reaction. Desirably the molar ratio will be at least 1:1, and more preferably the molar ratio will be at least 2.5:1, 10:1 or 50:1.

Host cells may be transformed by any means known in the art, including transfection, transduction, electroporation, etc. Selection of transformed cells is typically and conveniently carried out by a genetic selection means, although genetic and biochemical screening methods may also be employed.

In the case of Ty1 transposition, the use of the entire U3 or U5 terminal sequences has been found to be unnecessary. Thus as little as 4 bp of terminal sequence of U3 and/or U5 can be used. (The sequence of U3 and U5 are disclosed in FIG. 5 of reference 12). While there is some evidence that other unrelated sequences may be suitable as a substrate for integrase enzymes to generate single transposon-end joining products (14), such sequences may not be suitable for generating the two transposon-end, complete integration product necessary for the present invention.

Primers which are employed for sequencing according to the present invention are those which are known in the art for dideoxy-type sequencing. These are typically synthetic, single-stranded oligonucleotides of about 12–60 bases in length. It is desirable, according to the present invention that the primers for sequencing each flank of the inserted transposon be unique. Therefore, if the two transposon termini are identical, which they can be, the primer complementarity must extend into or be wholly derived from the "marker region" so that each primer only hybridizes to a single end of the transposon. Primers "complementary to a terminus of an artificial transposon" are those oligonucleotides which are 12 to 60 bases in length which are derived from the terminal approximately 150 bp of the artificial transposon. Primer sequences which are optimized for DNA sequencing can easily be designed into the artificial transposon.

Viral particles, according to the present invention are nucleoprotein complexes which are isolated from cellular extracts of infected cells. In the case of yeast retrotransposon Ty1, the particles are known as virus-like particles. An integrase activity can be purified from such particles using protein purification techniques known in the art. While Ty1 is exemplified in this application, it is believed that its closely related yeast retrotransposon Ty2 will be equally useful.

It has been found that divalent cations are necessary for transposition. Suitable concentrations of magnesium ions range from about 1 to about 50 mM. Preferably the concentration is between about 5 and 45 mM. The pH range which is suitable for in vitro transposition is broad, from pH 6 to 8, and may desirably be from pH 7 to pH 8.

In addition to the application of PART technology to the sequencing of DNA, there are a number of other applications which are possible, owing to the high efficiency and randomness of insertion of PARTs. Some of these are outlined below.

1. DNA Sequencing and Mapping i) Small-Scale DNA Sequencing.

Example: A 3.5 kb segment of DNA is cloned into a plasmid cloning vector. The investigators wish to obtain the complete nucleotide sequence of this 3.5 kb insert, on both strands using polymerase-based (Sanger) dideoxy sequencing. PART insertions are generated throughout the plasmid in vitro. The collection is screened by restriction mapping to determine whether individual PART insertions are located in the plasmid backbone or the insert, and a collection of target plasmids bearing insertions every 100–200 bp in the insert is recovered. Each PART is then used to sequence the DNA on both sides of the insertion, using unique primers homologous to the termini of the PART. Since standard dideoxy sequencing protocols lead to the recovery of 200–300 bp (or more) useful sequence information, the entire sequence of the 3.5 kb insert is recovered, on both strands.

ii) Large-Scale Sequencing.

Example: A yeast artificial chromosome (YAC), bacterial artificial chromosome (BAC), or other vehicle used for the propagation of large segments of DNA contains a large segment of human DNA that requires DNA sequence analysis. Assuming that a 400 kb YAC is used, the YAC is resolved on a pulsed field gel cast with low-melting point agar, and excised. PART insertions are generated in vitro within the YAC. A specialized PART derivative, containing a selectable yeast marker is used to enable the facile recovery of PART insertions by transforming the collection into yeast by protoplast fusion, with subsequent selection for complementation of an auxotrophy. PART insertions are recovered throughout the YAC in this manner. Each PART insertion is then used to recover sequence from the flanking DNA in both directions by cycle sequencing, using a thermostable polymerase. YACs bearing PART insertions are shotgun sequenced until the entire sequence is recovered. The original linkage of the sequence is maintained throughout the procedure, making data assimilation simpler than most large-scale sequencing methods. Finally, many aspects of this process are amenable to automation.

iii) DNA Mapping.

Using PART insertions such as those described above, a PART map could be constructed in a DNA segment of interest. Since the PART contains a number of useful restriction sites (6-bp and 8-bp cutters), the location of the insertions relative to the endpoints of the insert could be determined by cutting the clone with an enzyme such as Not I, and running the products on the appropriate gel. The sizes of the products would yield information about the location of the PART insertion relative to the ends and other sites such as known genes or Not I sites. The sequence information recovered from such a PART insertion could then be correlated with a map position. This approach enables the rapid assignment of a sequence tag to a map position, which would be a useful intermediate on the way to completing the entire sequence, especially if an entire genome is being sequenced. Another advantage is that the original linkage of the various map positions is maintained throughout the mapping procedure.

2. Gene Mapping by Integrative Disruption.

Example: A yeast gene has been cloned as part of a large, e.g., 15 kb DNA insert on a plasmid. The investigator wishes to know where, within this 15 kb, the gene is located. The clone was originally isolated by complementation of a mutant phenotype in yeast; hence, a functional assay for the presence of the gene exists. A set of PART insertions is made into the target plasmid and these are then transformed into yeast; non-complementing clones should contain insertions into the gene of interest. A selectable yeast gene (e.g., URA3, TRP1 or HIS3) could be incorporated into the artificial transposon, both simplifying the original selection in yeast for clones maintaining a transposon insertion, and allowing the facile identification of gene disrupter clones which could be later used directly to knock out the gene of interest in the host genome.

3. Introduction of any Functional or Non-Functional DNA Cis Element, Sequence, or Combination of Sequences into Another Segment of DNA.

i) Restriction Sites for Mapping, Making Deletions, Adding New DNA Fragments/Sequences.

Restriction enzymes are multipurpose tools. By inserting a site for a particular enzyme at a desired location, the site could be used for mapping, making deletions or adding restriction fragments to the target DNA.

Example 1: An artificial transposon containing two Not I restriction sites flanking a selectable marker is inserted into the target plasmid in vitro. Miniprep DNAs are screened by restriction mapping to locate an artificial transposon insertion in the desired region. Alternatively, an insertion library containing artificial transposon insertions throughout the target clone is screened with a junction oligonucleotide to identify an insertion at a particular phosphodiester bond. Once a suitably-positioned transposon is identified, the plasmid is cleaved with Not I, thus removing the majority of the transposon, and generating ends with a Not I restriction site. Since many sites flank the selectable marker in pAT-1 and pAT-2, this approach could be adapted for use with any pair of enzymes that would lead to the removal of the selectable gene and allow the subsequent cloning of an insert at the site. This general approach offers an alternative to creating a restriction endonuclease site by the method of site directed mutagenesis.

Example 2: A yeast artificial chromosome (YAC) containing 800 kb of human DNA is used as a target to generate artificial transposon insertions. Upon recovery of insertions, one is mapped to a position near a site thought to contain no functional genes. Since the artificial transposon contains a single Not I site and the chromosome lacks Not I sites, the unique site could be used to insert a novel gene into this location.

ii) Promoters, Enhancers, Terminators, Introns, Exons.

Example: An artificial transposon is created which contains the third exon of gene W which is known to encode a stretch of 99 prolines followed by 33 histidines and then 11 tyrosines. Normal mammalian 5' splice donor, 3' splice acceptor, and branch acceptor sites are incorporated into the transposon at the appropriate positions for correct splicing, along with a selectable marker. The transposon is integrated into gene X on a plasmid, and the plasmid subsequently transfected into mammalian cells in culture. The exon is found to be appropriately incorporated into the transcribed mRNA of gene X, with precise excision of all non-exon sequences. The protein chemistry of the region encoded by this exon is now studied in the new protein context.

iii) Drug-Selectable or Auxotrophic Markers Useful in Experimental and Non-Experimental Organisms Including: Bacteria, Plants, Yeast, Insects, Drosophila, Worms, Rodents, Humans, Mammals in General.

"Marker swap" or "Marker addition" transposons.

Goal: introduce or exchange genetic markers in a vector of interest, using the integration reaction rather than restriction enzymes. Transposons similar to the PART but containing different drug resistance (chloramphenicol, kanamycin) or yeast selectable markers (URA3, TRP1, HIS3, LEU2) between the transposon termini could be integrated into a target plasmid of choice. The resultant plasmids could be selected for the acquisition of the new marker and then if desired, be screened for loss of a pre-existing marker.

Example: You have a plasmid that contains a marker for ampicillin resistance as well as a gene of interest. For an upcoming experiment, you desire that the plasmid contain a chloramphenicol resistance marker, and require that the plasmid be lacking the ampicillin gene. Thus, the end goal is to have a single plasmid carrying your gene of interest, a chloramphenicol resistance marker, and no ampicillin resistance marker. To accomplish this, you perform an in vitro integration with an artificial transposon containing a chloramphenicol gene, and select plasmids that are chloramphenicol resistant. Next, you replica plate to ampicillin-containing plates, and identify chloramphenicol resistant/ampicillin sensitive clones. The new marker is found to have integrated within the Amp marker.

iv) Genes. Any gene of interest could be cloned into a pAT derivative and directly inserted as a transposon into a DNA target.

Example: A gene therapist wants to build a variety of new adenovirus constructs to test as delivery vehicles for the cystic fibrosis transmembrane regulator (CFTR) gene, which is the human gene responsible for cystic fibrosis. Since both the adenovirus genome and the CFTR cDNA are both quite large, strategies based on restriction enzymes are not easily identified. Instead, the gene therapist clones the CFTR cDNA driven by the CFTR promoter into a pAT derivative carrying a selectable marker, and inserts the resultant artificial transposon carrying the CFTR gene into the adenovirus vector. Thus, various constructs are rapidly built and tested.

v) Any Functional or Non-Functional DNA

DNA segments comprised of any nucleotide sequence or combination of sequences, could be envisioned to be incorporated into an artificial transposon, thus becoming amenable to recombination with a target via an integration reaction.

4. "Carry Along" Transposition.

An artificial transposon carries a drug-selectable marker/ or markers which allow selection of transposon-containing DNA target. The transposon also contains other DNA sequences adjacent to the marker (such as a gene). Hence, both the drug marker and the gene of interest are introduced upon integration of an artificial transposon with such a structure.

5. Fusion Protein Contracts.

An artificial transposon is designed such that, upon insertion into an open reading frame of a functional gene, a fusion protein would be produced. The fusion would be comprised of a portion of the original coding region of the functional gene, as well as a reporter which could be used to identify such active fusion proteins.

Example: An artificial transposon is created that contains the beta galactosidase gene. The reading frame is open from the terminus of the transposon through the beta galactosidase gene. Upon integration in a frame in a target gene, a fusion protein is produced that shows beta galactosidase activity.

6. Transgenic Constructs.

A drug-selectable marker useful in the organism under study is introduced into a desired region of a gene or DNA within a cloning vector, for the ultimate purpose of introducing the segment of DNA into the host genome. This general approach has been reported for bacteria, yeast, drosophila, C. elegans, and mouse, as well as other mammals, and includes integrative knockouts such as those reported by M. Capecchi's lab.

Example 1: A researcher wishes to examine a 20 kb segment of mouse DNA for possible promoter activity both in cultured cells and in the context of the organism. An artificial transposon containing a reporter gene such as Chloramphenicol acetyl transferase (CAT), luciferase, or β-galactosidase could be integrated into the 20 kb region, and screened by restriction mapping. Next, the insertions could be tested for expression in cell culture or muscle injection transient assays. Finally, constructs showing expression could be used to generate transgenic animals. Such animals could be used to study the expression conferred by the promoter, by assaying reporter activity in various tissues or developmental states.

Example 2: An artificial transposon is created which contains a human transcriptional enhancer element that functions only in heart muscle tissue during early heart development. By inserting copies of this transposon in the upstream, downstream, and intron regions of a gene of interest (cloned on a plasmid), constructs are generated where the gene would potentially be regulated by the enhancer in a tissue-specific and temporal manner. These constructs are used to generate transgenic animals where this gene would be expressed in this manner.

Example 3: Transgenic knockout constructs. An artificial transposon containing a NEO gene is created and integrated into a plasmid clone carrying the 5' portion of a gene of interest. The insertions are screened, and a single insertion occurring in the first exon of the gene, just downstream of the translation start codon AUG, is identified. The resulting construct is used directly to knockout the gene by generating a transgenic animal by ES technology. A second version would include the addition of a counterselectable marker at the 3' end of the construct to differentiate between homologous and non-homologous insertions. This counterselectable marker could be carried on a second artificial transposon. This general approach has been described by Capecchi and colleagues to generate "knockout mice" lacking the function of a particular gene.

EXAMPLES

Construction of pAT-1 pAT-1 (pSD544) and pAT-2 (pSD545) were constructed as follows. First, the plasmid pRS316 (ref. 15; a derivative of pBLUESCRIPT, Stratagene) was modified to eliminate the ampicillin resistance (amp$^r$) gene. This was accomplished by ligating together two fragments of pRS316 (a 2.1 kb Ssp I fragment and a 2.1 kb Bsa I/Ssp I fragment), thus creating the plasmid pSD528 which lacks a functional bla gene; this plasmid can be propagated in the pyrimidine-requiring E. coli strain MH1066 since the yeast URA3 gene on this construct complements the bacterial pyrF auxotrophy (16). pAT-1 and pAT-2 were constructed from plasmid pSD528 by replacing the pBLUESCRIPT multicloning site (mcs) (from the unique Kpn I site to the unique Sac I site) with polymerase chain reaction (PCR) adapters containing the appropriate sequences to create the structure indicated in FIG. 2. These PCR adapters were generated using primers SD112 (JB661) (5'- AAAA-GCTGGG-TACCGA-ACATGTT-CTCGAGGTCGACGGTATCG-3') and SD113 (JB662) (5'-GCGAATTGGA-GCTCGAAC-ATGTTCACCGC-GGTGG-CGGCCGCTC-3') with plasmids pBLUESCRIPT and pSD511 as templates. The resulting PCR products were digested with Kpn I and Sac I, and ligated to Kpn I/Sac I- digested pSD528 to generate pAT-1 and pAT-2. The structures of these constructs were confirmed by restriction mapping and sequence analysis.

In Vitro Reaction Conditions.

A typical in vitro DNA integration was carried out in a 20 $\mu$l reaction volume, and contained the following. 100–500 ng artificial transposon (0.8 kb), 1 $\mu$g CsCl-purified plasmid target (a 10 to 1 molar ratio of transposon to target), 2 $\mu$l 10× reaction buffer (150 mM MgCl$_2$, 100 mM Tris HCl, pH 7.5, 100 mM KCl, and 10 mM DTT), 5 $\mu$l 20% [w/v] PEG 8000, 2 $\mu$l VLPs, and water to 20 $\mu$l. The reaction was incubated at 30° Celsius for 30 minutes followed by 37° Celsius for 10 minutes, and then was terminated by adding 1.0 $\mu$l 0.5 M EDTA and heating to 65° Celsius for 20 minutes. Finally, the nucleic acids were phenol/chloroform extracted, ethanol precipitated, collected by centrifugation, washed with 70% ethanol, and resuspended in 10 $\mu$l TE (10 mM Tris, pH 8.0, 1 mM EDTA). 1 $\mu$l was used to transform 6 $\mu$l DH10B *E. coli* (Gibco/BRL) to drug resistance by electroporation.

PCR, Sequencing, Primers, Plasmid Constructions, CsCl Preps.

The PCR was carried out using reagents obtained from Perkin Elmer, as described (17). DNA sequencing was carried out using Sequenase (USB), and analyzed as described (18). Custom oligonucleotide primers were obtained from Operon Technologies, Inc. (Alameda, Calif.). The two primers used for sequencing from within the PART were SD111 (JB563) (5'-GACACTCTGTTA-TTACAAATCG-3') and SD110(JB532) (5'-GGTGATCCCTGAGCAGGTGG-3'). The integration site of each PART insertion was determined using either one or both of these primers, and analyzed with the aid of the Wisconsin GCG package. Plasmids were constructed using standard DNA cloning methods (19), and were purified from *E. coli* cultures by either STET miniprep (20) or alkaline lysis followed by CsCl banding (21).

Preparation of Artificial Transposons from pAT-1 and Derivatives.

20 $\mu$g of CsCl-purified plasmid DNA was digested with 50 units of Xmn I (Boehringer Mannhiem) for 4 hours at 37° Celsius. The resulting fragments were separated on a 1% agarose/TBE gel, and the transposon fragment was electroeluted from the gel using an IBI electroelution device.

Recovery of Clones Carrying Transposon Insertions Using Ampicillin/Trimethoprim Plates.

*E. coli* clones carrying plasmids with transposon insertions were identified by selection on M9 minimal plates (22) containing 1.0 mM thiamine HCl, 50 $\mu$g/ml ampicillin (Amp) and 100 $\mu$g/ml trimethoprim (Tri; Sigma). After one to two days incubation at 37° Celsius, the majority of colonies growing on M9/Amp/Tri plates contained plasmids with a transposon insertion. Dilutions of the transformation were routinely plated on LB plates containing 50 $\mu$g/ml Amp (22); this control monitored the number of target plasmids successfully carried through the procedure. When compared to the number of colonies on M9/Amp/Tri plates, the frequency of transposon insertion could be estimated (frequency of insertion=[# colonies on M9/Amp/Tri plates]/[# colonies on LB/Amp plates]). A positive control plasmid, pSD511, containing both Amp$^R$ and Tri$^R$ markers, routinely gave rise to equivalent numbers of colonies on LB/Amp (50 ug/ml), M9/Tri (100 ug/ml), or M9/Amp/Tri (50/100 ug/ml) plates under these conditions.

Transformation of *E. coli*.

The two strains transformed routinely in this work were DH5$\alpha$ (23) and DH10B (24). DH5$\alpha$ was prepared for electroporation as described (25), and electrocompetent DH10B cells were purchased from Gibco/BRL. Transformation by electroporation was accomplished for both strains using a Biorad Genepulser with 1 mm cuvettes and the following settings: capacitance: 25 $\mu$FD; voltage: 1.8 kV; and resistance: 200 ohms. Using pUC19 or pBLUESCRIPT as a test plasmid, freshly-prepared electrocompetent DH5$\alpha$ generally showed transformation efficiencies of $10^7$–$10^8$ colonies/$\mu$g DNA, whereas electrocompetent DH10B purchased from BRL/Gibco generally showed efficiencies of $5\times10^8$ to $5\times10^9$ colonies/$\mu$g DNA.

VLP Preparation.

VLPs were prepared from yeast cultures as described (26). Fractions from the final sucrose gradient containing integrase activity were aliquoted and frozen at $-70°$ Celsius where they were stable for more than 6 months.

In Vitro Integration of "Primer Island" Transposons into a Cloned Segment of Yeast Chromosome III Carried on a Plasmid Target.

We next generated PART insertions in vitro using various plasmid targets. One of the primary test clones consisted of a pRS200 backbone (a derivative of pBLUESCRIPT) with an 8.0 kb insert that spans bp 136,155 to 144,333 of yeast chromosome III; this plasmid is called p76-2. With a single in vitro integration reaction, we recovered approximately 13,000 PART insertions in p76-2 (Table 1).

TABLE 1

Recovery of PART insertions into clone 76-2.

| Rxn | EDTA[a] | Total transformants[b] | Total insertion plasmids[c] | Frequency of transposition[d] |
|---|---|---|---|---|
| 1. | − | 0 | 0 | — |
| 2. | − | $3.1 \times 10^8$ | $4.5 \times 10^8$ | — |
| 3. | − | $3.1 \times 10^8$ | $1.3 \times 10^4$ | $4.2 \times 10^{-5}$ |
| 4. | + | $5.7 \times 10^8$ | $5.0 \times 10^2$ | $9.1 \times 10^{-7}$ |

Reaction 1) negative transformation control (no DNA added); 2) positive transformation control (pSD511, which contains both Amp$^R$ and Tri$^R$ markers); 3) complete integration reaction using p76-2 as the target; 4) same as reaction 3, but EDTA was added (inhibits integrase activity).
[a]+, EDTA added to 25 mM
[b]Total number of Amp$^R$ transformants
[c]Total number of Amp$^R$/Tri$^R$ transformants
[d]Number of transpositions into target plasmid (Amp$^R$/Tri$^R$ colonies) divided by the total number of transformants (Amp$^R$ colonies)

By measuring the number of colonies transformed to ampicillin resistance vs. combined trimethoprim and ampicillin resistance, we determined that the frequency of transposon insertion recovery was approximately $4.2\times10^{-5}$ (i.e., 1 insertion per $2.4\times10^4$ target molecules; Table 1). Although this frequency is not likely to represent the upper limits of optimization, it is sufficiently high that a large number of insertion events are readily recovered, while sufficiently low that a single target is generally limited to a single transposon insertion (two transposon insertions in a single target might be useful for some purposes, but would render the molecule useless as a sequencing template).

Analysis of 156 randomly chosen Amp$^R$/Tri$^R$ colonies indicated that PART insertions occurred into all areas of the plasmid target, including both the pRS200 backbone (6.0 kb) and the 8.0 kb chromosome III insert, as determined by restriction mapping and/or sequence analysis (Table 2).

TABLE 2

Examination of Tri^R/Amp^R colonies from a single in vitro integration reaction.

|  |  | % |
|---|---|---|
| Total number of Tri^R clones examined | 156 | 100 |
| # minipreps recovered | 153 | 98 |
| # easily-identifiable insertions | 134 | 86 |
| In insert | 78 | 50 |
| In vector | 56 | 36 |
| Other | 19 | 12 |
| double insertions/cotransformants[a] | 13 | 8 |
| unknown plasmid map | 5 | 3 |
| no transposon | 1 | <1 |

[a] This class contains some plasmids that apparently had two independent insertions in the target as determined by restriction mapping, and others with DNA sequence that was readable to the insertion junction, at which point two superimposed sequences were observed.

More than 86% of these 156 clones (134) had easily-identifiable PART insertions; of these, 78 (50%) were in the cloned 8 kb insert, while 56 (36%) were in the vector. A small percentage of the clones were found to have two superimposed restriction maps/and or sequences. There are several likely explanations for this result, including the possibility that two plasmids transformed a single *E. coli* clone, or that two transposon insertions occurred into a single plasmid target; the available evidence indicates that most of these clones are explained by such mechanisms. Hence, a small portion of clones recovered from an in vitro integration reaction would not be suitable for direct DNA sequence analysis for this reason (12% in this example, Table 2). Likewise, vector insertions would not be useful for sequencing the insert. Nevertheless, one of every two Amp^R/Tri^R colonies analyzed from this single reaction could be used directly to obtain DNA sequence from the cloned insert. Furthermore, analysis of only 156 minipreps led to the assembly of 78 useful insertions in an 8 kb insert, corresponding to an expected distribution of roughly one insertion per 100 bp.

The distribution of individual insertions of the artificial transposon relative to adjacent insertions is shown in Table 3.

TABLE 3

Tabulation of PART insertion data from plasmid target p76-2

| Insertion Plasmid | Insertion point in p76-2 (chr III numbering) | distance to 5-primeclone |
|---|---|---|
| 5-prime end | 136155 | — |
| 151 | 136394 R | 239 |
| 72 | 136397 F | 3 |
| 25 | 136415 R | 18 |
| 116 | 136425 R | 10 |
| 107 | 136460 R | 35 |
| 93 | 136576 R | 16 |
| 155 | 136611 F | 35 |
| 135 | 136685 F | 74 |
| 46 | 136724 R | 39 |
| 141 | 136767 F | 43 |
| 84 | 136832 R | 65 |
| 33 | 137058 F | 226 |
| 70 | 137165 F | 107 |
| 124 | 137192 R | 27 |
| 101 | 137347 R | 155 |
| 59 | 137451 F | 104 |
| 17 | 137622 R | 171 |
| 77 | 137657 F | 35 |
| 89 | 137811 F | 154 |
| 147 | 137879 R | 68 |
| 54 | 138127 R | 248 |
| 145 | 138161 F | 34 |
| 105 | 138175 F | 14 |
| 16 | 138263 R | 88 |
| 146 | 138345 F | 82 |
| 20 | 138503 F | 158 |
| 122 | 138581 R | 78 |
| 63 | 138587 F | 6 |
| 125 | 138588 F | 1 |
| 86 | 138618 R | 30 |
| 152 | 138702 F | 84 |
| 110 | 138720 F | 18 |
| 32 | 138747 R | 27 |
| 117 | 138771 F | 24 |
| 114 | 138819 R | 48 |
| 94 | 138905 R | 86 |
| 40 | 138906 R | 1 |
| 112 | 139283 R | 377 |
| 41 | 139291 R | 8 |
| 119 | 139332 R | 41 |
| 102 | 139529 F | 197 |
| 19 | 139551 R | 22 |
| 134 | 139690 R | 139 |
| 85 | 139863 R | 173 |
| 42 | 139980 R | 117 |
| 22 | 140052 R | 72 |
| 73 | 140176 R | 124 |
| 80 | 140259 R | 83 |
| 38 | 140360 F | 101 |
| 90 | 140446 R | 86 |
| 103 | 140794 R | 348 |
| 24 | 141023 R | 229 |
| 57 | 141024 R | 1 |
| 2 | 141074 R | 50 |
| 49 | 141174 F | 100 |
| 11 | 141412 F | 238 |
| 68 | 141633 F | 221 |
| 58 | 141765 F | 132 |
| 12 | 141770 R | 5 |
| 142 | 141836 F | 66 |
| 29 | 141876 F | 40 |
| 69 | 142015 R | 139 |
| 31 | 142027 R | 12 |
| 4 | 142094 R | 67 |
| 78 | 142180 F | 86 |
| 60 | 142226 R | 46 |
| 127 | 142382 R | 156 |
| 3 | 142551 R | 169 |
| 74 | 142713 F | 162 |
| 108 | 142820 F | 107 |
| 6 | 143141 F | 321 |
| 109 | 143165 R | 24 |
| 149 | 143333 R | 163 |
| 27 | 143616 F | 283 |
| 39 | 143856 F | 240 |
| 51 | 143921 F | 65 |
| 13 | 144076 F | 155 |
| 66 | 144127 F | 51 |
| 3-prime end | 144333 | 206 |

Statistics on insertions
n = 78
Mean interval distance = 102.3 +/−88.1
Insertions/kb for each 1 kb of target:

| Region of target | Number of insertions per kb target DNA |
|---|---|
| 136,155 to 137,000 | 13 |
| 137,000 to 138,000 | 9 |
| 138,000 to 139,000 | 17 |
| 139,000 to 140,000 | 14 |
| 140,000 to 141,000 | 6 |
| 141,000 to 142,000 | 10 |
| 142,000 to 143,000 | 9 |

TABLE 3-continued

Tabulation of PART insertion data from plasmid target p76-2

| 143,000 to 144,000 | 6 |
| 144,000 to 144,333 | 6 |

Mean number of insertions per kb target DNA = 10.2 +/−3.7
Orientation
Forward 34 (44%)
Reverse 44 (56%)

Since the entire yeast chromosome III sequence has been previously determined (27), we could easily identify the precise sites of transposon integration by determining the nucleotide sequences at the insertion junctions. Indeed, the 78 PART insertions were found to be distributed throughout the entire 8 kb insert (FIG. 3). A little less than half of these insertions were in the forward orientation (34/78 or 44%), indicating a slight orientation bias for this target. However, since primer extensions can be initiated into the sequences flanking the insertion on both sides irrespective of the PART orientation, an orientation bias does not affect the utility of the PART insertion for purposes of DNA sequencing. The mean distance between adjacent insertions was 102.3±88.1 overall. Only six of the intervals were greater than 250 bp, and the largest of these was only 377 bp. Hence, the vast majority of the intervals between adjacent transposon insertions were well below the maximum distance that can be reached with an average primer extension under sequencing conditions. A property of Ty1 integrase is that it creates characteristic 5 bp target sequence duplications flanking the insertion site upon integration (10–12, 28). As expected, 5 bp target site duplications were found at each PART integration site examined (only a small portion of the insertions were sequenced at both ends in this example). No deletions or rearrangements were observed.

A conceptual primer extension contig map based on our results is shown in FIG. 4. We have made the assumption that each primer extension would lead to the successful recovery of 250 bp of useful sequence information. 100% of the sequence would be recovered on one strand or the other using the 78 PART insertions shown in FIG. 3. Only 6 gaps (3 on the top strand, and 3 on the bottom; each <150 bp) would exist. But because the two initial primer extensions flanking such a gap would cross in the middle on opposite strands, uninterrupted DNA sequence would be recovered on one strand or the other. Nevertheless, the gaps on the remaining strand could be closed with either: i) additional PART insertions in the necessary regions, identified with appropriate restriction mapping, ii) custom primers, or iii) longer sequencing runs. Of course, we have made the assumption that only 250 bp of sequence information can be recovered from a single primer extension; in fact, greater than 400 is routinely obtained with automated sequencers, and 800 to 1000 is becoming possible with automated sequencers in development. Hence, if the mean readable sequence is extended to 400 bp, 100% of the sequence could be easily recovered using fewer than 78 PART insertions. Other Targets Tested.

In addition to clone 76-2 containing a DNA insert from yeast chromosome III, we have tested other plasmid targets. These plasmids had a variety of backbone structures and carried various cloned inserts (Table 3). The backbones included pUC19 and pBLUESCRIPT as well as others, and the DNA inserts originated from different species including yeast and human. In each case, results similar to those shown for clone 76-2 were obtained: i) insertions were mapped to all regions of these targets, ii) a large number of insertions was readily recovered from reactions using each target, and iii) recovered insertions consistently served as successful sequencing templates. Moreover, in two cases other than p76-2 (pCAR143 and pWAF-1; table 3), this system was used to recover 90–100% of the nucleotide sequence from clones with previously unknown sequences. Hence, in vitro integration of artificial transposons is expected to work well with most or all plasmid targets, making it both a generally useful sequencing tool and a general method of integrating new DNA sequences into plasmid targets to generate recombinant DNA molecules.

REFERENCES

1. Smith, L. M. (1993) *Science* 262, 530–531.
2. Itakura, K., Rossi, J. J., and Wallace, R. B. (1984) *Ann. Rev. Biochem.* 53, 323–356.
3. Sambrook, J., Fritch, E. F., and Maniatis, T. (1989) *Molecular Cloning A Laboratory Manual, Second Edition*. Cold Spring Harbor Laboratory Press, Cold Spring Harbor, N.Y. pp 13.2–13.104.
4. Sulston, J., Du, Z., Thomas, K., Wilson, R., Hillier, L, Staden, R., and etc. (1992) *Nature* 356, 37–41.
5. Ausubel, F. M., Brent, R., Kingston, R. E., Moore, D. D., Seidman, J. G., Smith, J. A., and Struhl, K. (1989) *Current Protocols in Molecular Biology* 1, 7.2.1–7.2.20.
6. Strathman, M., Hamilton, B. A., Mayeda, C. A., Simon, M. I., Meyerowitz, E. M., and Palazzolo, M. J. (1991) *Proc. Natl. Acad. Sci. USA* 88, 1247–1250.
7. Phadnis, S. H., Huang, H. V., and Berg, D. E. (1989) *Proc. Natl. Acad. Sci. USA* 86, 5908–5912.
8. Way, J. C., Davis, M. A., Morisato, D., Roberts, D. E., and Kleckner, N. (1984) *Gene* 32, 369–379.
9. Kleckner, N., Bender, J., and Gottesman, S. (1991) *Methods Enzymol.* 204, 139–180.
9a. Lee, F. Y., Butler, D., and Kleckner, N. (1987) *Proc. Natl. Acad. Sci. USA* 84, 7876- .
10. Brown, P. O., Bowerman, B., Varmus, H. E., and Bishop, J. M. (1987) *Cell* 49, 347–356.
11. Eichinger, D. J. and Boeke, J. D. (1988) *Cell* 54, 955–966.
12. Eichinger, D. J. and Boeke, J. D. (1990) *Genes Dev.* 4, 324–330.
13. Braiterman, L. and Boeke, J. D. (1994) *Mol. Cell. Biol.*, in press.
14. Braiterman, L. and Boeke, J. D. (1994) *Mol. Cell. Biol.*, in press.
15. Sikorski, R. S., and Hieter, P. (1989) *Genetics* 122, 19–27.
16. Sikorski, R. S., and Boeke, J. D. (1991) *Methods Enzymol.* 194, 302–318.
17. Innis, M. A., and Gelfand, D. H. (1990) In: *PCR Protocols A Guide to Methods and Applications*. Academic Press, Inc., San Diego, Calif. pp 3–12.
18. Sanger, F., Nicklen, S., and Coulson, A. R. (1977) *Proc. Natl. Acad. Sci. USA* 74, 5463–5467.
19. Sambrook, J., Fritch, E. F., and Maniatis, T. (1989) *Molecular Cloning A Laboratory Manual, Second Edition*. Cold Spring Harbor laboratory Press, Cold Spring Harbor, N.Y. pp 1.53–1.110.
20. Holmes, D. S., and Quigley, M. (1981) *Anal. Biochem.* 114, 193–197.
21. Ausubel, F. M., Brent, R., Kingston, R. E., Moore, D. D., Seidman, J. G., Smith, J. A., and Struhl, K. (1989) *Current Protocols in Molecular Biology* 1, 1.7.1–1.7.11.
22. Maniatis, T., Fritsch, E. F., and Sambrook, J. (1982) *Molecular Cloning A Laboratory Manual*. Cold Spring Harbor Laboratory Press, Cold Spring Harbor, N.Y. pp68–69.

23. Hanahan, D. (1983) *J. Mol. Biol.* 166, 557–580.
24. Calvin, N. M., and Hanawalt, P. C. (1988) *J. Bacteriol.* 170, 2796–2801.
25. Ausubel, F. M., Brent, R., Kingston, R. E., Moore, D. D., Seidman, J. G., Smith, J. A., and Struhl, K. (1989) *Current Protocols in Molecular Biology* 1, 1.8.4–1.8.8.
26. Braiterman, L. T., Monakian, G. M., Eichinger, D. J., Merbs, S. L., Gabriel, A., and Boeke, J. D. (1994) *Gene,* in press.
27. Oliver, S. G., van der Aart, Q. J. M., Agostoni-Carbone, M. L., Aigle, M., Alberghina, L., and etc. (1992) *Nature* 357, 38–46.
28. Ji, H., Moore, D. P., Blomberg, M. A., Braiterman, L. T., Voytas, D. F., Natsoulis, G., and Boeke, J. D. (1993) *Cell* 73, 1007–1018.
29. Bushman, F. D., and Craigie, R. (1991) *Proc. Natl. Acad. Sci. USA* 88, 1339–1343.

We claim:

1. A kit for DNA sequencing, comprising:

an artificial transposon having termini which are substrates for yeast retrotransposon Ty1 integrase;

yeast retrotransposon Ty1 integrase;

a buffer for in vitro transposition of said artificial transposon, said buffer having a pH of 6 to 8 and 1 to 50 mM $Mg^{+2}$; and a primer which is complementary to a terminus of said artificial transposon.

2. The kit of claim 1 wherein said integrase is supplied as Ty1 virus-like particles.

3. The kit of claim 1 wherein said artificial transposon is isolated with a restriction enzyme which creates blunt ends.

4. The kit of claim 3 wherein said restriction enzyme is Xmn I.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 4164 base pairs
      (B) TYPE: nucleic acid
      (C) STRANDEDNESS: double
      (D) TOPOLOGY: circular (ii) MOLECULE TYPE: DNA (genomic)

(iii) HYPOTHETICAL: NO (iv) ANTI-SENSE: NO (vii) IMMEDIATE SOURCE:
      (B) CLONE: pAT-1

(xi) SEQUENCE DESCRIPTION: SEQ ID NO:1:

```
TCGCGCGTTT CGGTGATGAC GGTGAAAACC TCTGACACAT GCAGCTCCCG GAGACGGTCA      60

CAGCTTGTCT GTAAGCGGAT GCCGGGAGCA GACAAGCCCG TCAGGGCGCG TCAGCGGGTG     120

TTGGCGGGTG TCGGGCTGG CTTAACTATG CGGCATCAGA GCAGATTGTA CTGAGAGTGC      180

ACCATACCAC AGCTTTTCAA TTCAATTCAT CATTTTTTTT TTATTCTTTT TTTTGATTTC     240

GGTTTCTTTG AAATTTTTTT GATTCGGTAA TCTCCGAACA GAAGGAAGAA CGAAGGAAGG     300

AGCACAGACT TAGATTGGTA TATATACGCA TATGTAGTGT TGAAGAAACA TGAAATTGCC     360

CAGTATTCTT AACCCAACTG CACAGAACAA AAACCTGCAG GAAACGAAGA TAAATCATGT     420

CGAAAGCTAC ATATAAGGAA CGTGCTGCTA CTCATCCTAG TCCTGTTGCT GCCAAGCTAT     480

TTAATATCAT GCACGAAAAG CAAACAAACT TGTGTGCTTC ATTGGATGTT CGTACCACCA     540

AGGAATTACT GGAGTTAGTT GAAGCATTAG GTCCCAAAAT TTGTTTACTA AAAACACATG     600

TGGATATCTT GACTGATTTT TCCATGGAGG GCACAGTTAA GCCGCTAAAG GCATTATCCG     660

CCAAGTACAA TTTTTTACTC TTCGAAGACA GAAAATTTGC TGACATTGGT AATACAGTCA     720

AATTGCAGTA CTCTGCGGGT GTATACAGAA TAGCAGAATG GGCAGACATT ACGAATGCAC     780

ACGGTGTGGT GGGCCCAGGT ATTGTTAGCG GTTTGAAGCA GGCGGCAGAA GAAGTAACAA     840

AGGAACCTAG AGGCCTTTTG ATGTTAGCAG AATTGTCATG CAAGGGCTCC CTATCTACTG     900

GAGAATATAC TAAGGGTACT GTTGACATTG CGAAGAGCGA CAAAGATTTT GTTATCGGCT     960

TTATTGCTCA AAGAGACATG GGTGGAAGAG ATGAAGGTTA CGATTGGTTG ATTATGACAC    1020

CCGGTGTGGG TTTAGATGAC AAGGGAGACG CATTGGGTCA ACAGTATAGA ACCGTGGATG    1080

ATGTGGTCTC TACAGGATCT GACATTATTA TTGTTGGAAG AGGACTATTT GCAAAGGGAA    1140

GGGATGCTAA GGTAGAGGGT GAACGTTACA GAAAAGCAGG CTGGGAAGCA TATTTGAGAA    1200

GATGCGGCCA GCAAAACTAA AAAACTGTAT TATAAGTAAA TGCATGTATA CTAAACTCAC    1260
```

```
AAATTAGAGC TTCAATTTAA TTATATCAGT TATTACCCTA TGCGGTGTGA ATACCGCAC      1320

AGATGCGTAA GGAGAAAATA CCGCATCAGG AAATTGTAAA CGTTAATATT TTGTTAAAAT     1380

TCGCGTTAAA TTTTTGTTAA ATCAGCTCAT TTTTTAACCA ATAGGCCGAA ATCGGCAAAA     1440

TCCCTTATAA ATCAAAAGAA TAGACCGAGA TAGGGTTGAG TGTTGTTCCA GTTTGGAACA     1500

AGAGTCCACT ATTAAAGAAC GTGGACTCCA ACGTCAAAGG GCGAAAAACC GTCTATCAGG     1560

GCGATGGCCC ACTACGTGAA CCATCACCCT AATCAAGTTT TTTGGGGTCG AGGTGCCGTA     1620

AAGCACTAAA TCGGAACCCT AAAGGGAGCC CCCGATTTAG AGCTTGACGG GGAAAGCCGG     1680

CGAACGTGGC GAGAAAGGAA GGGAAGAAAG CGAAAGGAGC GGGCGCTAGG GCGCTGGCAA     1740

GTGTAGCGGT CACGCTGCGC GTAACCACCA CACCCGCCGC GCTTAATGCG CCGCTACAGG     1800

GCGCGTCGCG CCATTCGCCA TTCAGGCTGC GCAACTGTTG GGAAGGGCGA TCGGTGCGGG     1860

CCTCTTCGCT ATTACGCCAG CTGGCGAAAG GGGGATGTGC TGCAAGGCGA TTAAGTTGGG     1920

TAACGCCAGG GTTTTCCCAG TCACGACGTT GTAAAACGAC GGCCAGTGAA TTGTAATACG     1980

ACTCACTATA GGGCGAATTG GAGCTCGAAC ATGTTCACCG CGGTGGCGGC CGCTCTAGAA     2040

CTAGTGGATC CCCCGGGCTG CAGGAATTCG ATATCAAGCT TATCGATACC GTCGACCTCG     2100

AGAACATGTT CGGTACCAGC TTTTGTTCCC TTTAGTGAGG GTTAATTCCG AGCTTGGCGT     2160

AATCATGGTC ATAGCTGTTT CCTGTGTGAA ATTGTTATCC GCTCACAATT CCACACAACA     2220

TACGAGCCGG AAGCATAAAG TGTAAAGCCT GGGGTGCCTA ATGAGTGAGG TAACTCACAT     2280

TAATTGCGTT GCGCTCACTG CCCGCTTTCC AGTCGGGAAA CCTGTCGTGC CAGCTGCATT     2340

AATGAATCGG CCAACGCGCG GGGAGAGGCG GTTTGCGTAT TGGGCGCTCT TCCGCTTCCT     2400

CGCTCACTGA CTCGCTGCGC TCGGTCGTTC GGCTGCGGCG AGCGGTATCA GCTCACTCAA     2460

AGGCGGTAAT ACGGTTATCC ACAGAATCAG GGGATAACGC AGGAAAGAAC ATGTGAGCAA     2520

AAGGCCAGCA AAAGGCCAGG AACCGTAAAA AGGCCGCGTT GCTGGCGTTT TTCCATAGGC     2580

TCCGCCCCCC TGACGAGCAT CACAAAAATC GACGCTCAAG TCAGAGGTGG CGAAACCCGA     2640

CAGGACTATA AAGATACCAG GCGTTTCCCC CTGGAAGCTC CCTCGTGCGC TCTCCTGTTC     2700

CGACCCTGCC GCTTACCGGA TACCTGTCCG CCTTTCTCCC TTCGGGAAGC GTGGCGCTTT     2760

CTCATAGCTC ACGCTGTAGG TATCTCAGTT CGGTGTAGGT CGTTCGCTCC AAGCTGGGCT     2820

GTGTGCACGA ACCCCCCGTT CAGCCCGACC GCTGCGCCTT ATCCGGTAAC TATCGTCTTG     2880

AGTCCAACCC GGTAAGACAC GACTTATCGC CACTGGCAGC AGCCACTGGT AACAGGATTA     2940

GCAGAGCGAG GTATGTAGGC GGTGCTACAG AGTTCTTGAA GTGGTGGCCT AACTACGGCT     3000

ACACTAGAAG GACAGTATTT GGTATCTGCG CTCTGCTGAA GCCAGTTACC TTCGGAAAAA     3060

GAGTTGGTAG CTCTTGATCC GGCAAACAAA CCACCGCTGG TAGCGGTGGT TTTTTTGTTT     3120

GCAAGCAGCA GATTACGCGC AGAAAAAAAG GATCTCAAGA AGATCCTTTG ATCTTTTCTA     3180

CGGGGTCTGA CGCTCAGTGG AACGAAAACT CACGTTAAGG GATTTTGGTC ATGAGATTAT     3240

CAAAAAGGAT CTTCACCTAG ATCCTTTTAA ATTAAAAATG AAGTTTTAAA TCAATCTAAA     3300

GTATATATGA GTAAACTTGG TCTGACAGTT ACCAATGCTT AATCAGTGAG GCACCTATCT     3360

CAGCGATCTG TCTATTTCGT TCATCCATAG TTGCCTGACT CCCCGTCGTG TAGATAACTA     3420

CGATACGGGA GGGCTTACCA TCTGGCCCCA GTGCTGCAAT GATACCGATT ATTGAAGCAT     3480

TTATCAGGGT TATTGTCTCA TGAGCGGATA CATATTTGAA TGTATTTAGA AAAATAAACA     3540

AATAGGGGTT CCGCGCACAT TTCCCCGAAA AGTGCCACCT GGGTCCTTTT CATCACGTGC     3600

TATAAAAATA ATTATAATTT AAATTTTTTA ATATAAATAT ATAAATTAAA AATAGAAAGT     3660
```

-continued

```
AAAAAAAGAA ATTAAAGAAA AAATAGTTTT TGTTTTCCGA AGATGTAAAA GACTCTAGGG    3720

GGATCGCCAA CAAATACTAC CTTTTATCTT GCTCTTCCTG CTCTCAGGTA TTAATGCCGA    3780

ATTGTTTCAT CTTGTCTGTG TAGAAGACCA CACACGAAAA TCCTGTGATT TTACATTTTA    3840

CTTATCGTTA ATCGAATGTA TATCTATTTA ATCTGCTTTT CTTGTCTAAT AAATATATAT    3900

GTAAAGTACG CTTTTTGTTG AAATTTTTTA AACCTTTGTT TATTTTTTTT TCTTCATTCC    3960

GTAACTCTTC TACCTTCTTT ATTTACTTTC TAAAATCCAA ATACAAAACA TAAAAATAAA    4020

TAAACACAGA GTAAATTCCC AAATTATTCC ATCATTAAAA GATACGAGGC GCGTGTAAGT    4080

TACAGGCAAG CGATCCGTCC TAAGAAACCA TTATTATCAT GACATTAACC TATAAAAATA    4140

GGCGTATCAC GAGGCCCTTT CGTC                                          4164
```

(2) INFORMATION FOR SEQ ID NO:2:

(i) SEQUENCE CHARACTERISTICS:
        (A) LENGTH: 4933 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (iv) ANTI-SENSE: NO (vii) IMMEDIATE SOURCE:
        (B) CLONE: pAT-2

(xi) SEQUENCE DESCRIPTION: SEQ ID NO:2:

```
TCGCGCGTTT CGGTGATGAC GGTGAAAACC TCTGACACAT GCAGCTCCCG GAGACGGTCA      60

CAGCTTGTCT GTAAGCGGAT GCCGGGAGCA GACAAGCCCG TCAGGGCGCG TCAGCGGGTG     120

TTGGCGGGTG TCGGGCTGG CTTAACTATG CGGCATCAGA GCAGATTGTA CTGAGAGTGC      180

ACCATACCAC AGCTTTTCAA TTCAATTCAT CATTTTTTTT TTATTCTTTT TTTTGATTTC     240

GGTTTCTTTG AAATTTTTTT GATTCGGTAA TCTCCGAACA GAAGGAAGAA CGAAGGAAGG     300

AGCACAGACT TAGATTGGTA TATATACGCA TATGTAGTGT TGAAGAAACA TGAAATTGCC     360

CAGTATTCTT AACCCAACTG CACAGAACAA AAACCTGCAG GAAACGAAGA TAAATCATGT     420

CGAAAGCTAC ATATAAGGAA CGTGCTGCTA CTCATCCTAG TCCTGTTGCT GCCAAGCTAT     480

TTAATATCAT GCACGAAAAG CAAACAAACT TGTGTGCTTC ATTGGATGTT CGTACCACCA     540

AGGAATTACT GGAGTTAGTT GAAGCATTAG GTCCCAAAAT TGTTTACTA AAAACACATG      600

TGGATATCTT GACTGATTTT TCCATGGAGG GCACAGTTAA GCCGCTAAAG GCATTATCCG     660

CCAAGTACAA TTTTTTACTC TTCGAAGACA GAAAATTTGC TGACATTGGT AATACAGTCA     720

AATTGCAGTA CTCTGCGGGT GTATACAGAA TAGCAGAATG GGCAGACATT ACGAATGCAC     780

ACGGTGTGGT GGGCCCAGGT ATTGTTAGCG GTTTGAAGCA GGCGGCAGAA GAAGTAACAA     840

AGGAACCTAG AGGCCTTTTG ATGTTAGCAG AATTGTCATG CAAGGGCTCC CTATCTACTG     900

GAGAATATAC TAAGGGTACT GTTGACATTG CGAAGAGCGA CAAAGATTTT GTTATCGGCT     960

TTATTGCTCA AAGAGACATG GGTGGAAGAG ATGAAGGTTA CGATTGGTTG ATTATGACAC    1020

CCGGTGTGGG TTTAGATGAC AAGGGAGACG CATTGGGTCA ACAGTATAGA ACCGTGGATG    1080

ATGTGGTCTC TACAGGATCT GACATTATTA TTGTTGGAAG AGGACTATTT GCAAAGGGAA    1140

GGGATGCTAA GGTAGAGGGT GAACGTTACA GAAAAGCAGG CTGGGAAGCA TATTTGAGAA    1200

GATGCGGCCA GCAAAACTAA AAAACTGTAT TATAAGTAAA TGCATGTATA CTAAACTCAC    1260
```

```
AAATTAGAGC TTCAATTTAA TTATATCAGT TATTACCCTA TGCGGTGTGA ATACCGCAC      1320

AGATGCGTAA GGAGAAAATA CCGCATCAGG AAATTGTAAA CGTTAATATT TTGTTAAAAT      1380

TCGCGTTAAA TTTTTGTTAA ATCAGCTCAT TTTTTAACCA ATAGGCCGAA ATCGGCAAAA      1440

TCCCTTATAA ATCAAAAGAA TAGACCGAGA TAGGGTTGAG TGTTGTTCCA GTTTGGAACA      1500

AGAGTCCACT ATTAAAGAAC GTGGACTCCA ACGTCAAAGG GCGAAAAACC GTCTATCAGG      1560

GCGATGGCCC ACTACGTGAA CCATCACCCT AATCAAGTTT TTTGGGGTCG AGGTGCCGTA      1620

AAGCACTAAA TCGGAACCCT AAAGGGAGCC CCCGATTTAG AGCTTGACGG GGAAAGCCGG      1680

CGAACGTGGC GAGAAAGGAA GGGAAGAAAG CGAAAGGAGC GGGCGCTAGG GCGCTGGCAA      1740

GTGTAGCGGT CACGCTGCGC GTAACCACCA CACCCGCCGC GCTTAATGCG CCGCTACAGG      1800

GCGCGTCGCG CCATTCGCCA TTCAGGCTGC GCAACTGTTG GGAAGGGCGA TCGGTGCGGG      1860

CCTCTTCGCT ATTACGCCAG CTGGCGAAAG GGGGATGTGC TGCAAGGCGA TTAAGTTGGG      1920

TAACGCCAGG GTTTTCCCAG TCACGACGTT GTAAAACGAC GGCCAGTGAA TTGTAATACG      1980

ACTCACTATA GGGCGAATTG GAGCTCGAAC ATGTTCACCG CGGTGGCGGC CGCTCTAGAA      2040

CTAGTGGATC CTGCAAGCAG GATAGACGGC ATGCACGATT TGTAATAACA GAGTGTCTTG      2100

TATTTTTAAA GAAAGTCTAT TTAATACAAG TGATTATATT AATTAACGGT AAGCATCAGC      2160

GGGTGACAAA ACGAGCATGC TTACTAATAA AATGTTAACC TCTGAGGAAG AATTGTGAAA      2220

CTATCACTAA TGGTAGCTAT ATCGAAGAAT GGAGTTATCG GGAATGGCCC TGATATTCCA      2280

TGGAGTGCCA AAGGTGAACA GCTCCTGTTT AAAGCTATTA CCTATAACCA ATGGCTGTTG      2340

GTTGGACGCA AGACTTTTGA ATCAATGGGA GCATTACCCA ACCGAAAGTA TGCGGTCGTA      2400

ACACGTTCAA GTTTTACATC TGACAATGAG AACGTATTGA TCTTTCCATC AATTAAAGAT      2460

GCTTTAACCA ACCTAAAGAA AATAACGGAT CATGTCATTG TTTCAGGTGG TGGGAGATA      2520

TACAAAAGCC TGATCGATCA AGTAGATACA CTACATATAT CTACAATAGA CATCGAGCCG      2580

GAAGGTGATG TTTACTTTCC TGAAATCCCC AGCAATTTTA GGCCAGTTTT TACCCAAGAC      2640

TTCGCCTCTA ACATAAATTA TAGTTACCAA ATCTGGCAAA AGGGTTAACA AGTGGCAGCA      2700

ACGGATTCGC AAACCTGTCA CGCCTTTTGT GCCAAAAGCC GCGCCAGGTT TGCGATCCGC      2760

TGTGCCAGGC GTTAGGCGTC ATATGAAGAT TTCGGTGATC CCTGAGCAGG TGGCGGAAAC      2820

ATTGGATGCT GAGAATTCGA TATCAAGCTT ATCGATACCG TCGACCTCGA GAACATGTTC      2880

GGTACCAGCT TTTGTTCCCT TTAGTGAGGG TTAATTCCGA GCTTGGCGTA ATCATGGTCA      2940

TAGCTGTTTC CTGTGTGAAA TTGTTATCCG CTCACAATTC CACACAACAT ACGAGCCGGA      3000

AGCATAAAGT GTAAAGCCTG GGGTGCCTAA TGAGTGAGGT AACTCACATT AATTGCGTTG      3060

CGCTCACTGC CCGCTTTCCA GTCGGGAAAC CTGTCGTGCC AGCTGCATTA ATGAATCGGC      3120

CAACGCGCGG GGAGAGGCGG TTTGCGTATT GGGCGCTCTT CCGCTTCCTC GCTCACTGAC      3180

TCGCTGCGCT CGGTCGTTCG GCTGCGGCGA GCGGTATCAG CTCACTCAAA GGCGGTAATA      3240

CGGTTATCCA CAGAATCAGG GGATAACGCA GGAAAGAACA TGTGAGCAAA AGGCCAGCAA      3300

AAGGCCAGGA ACCGTAAAAA GGCCGCGTTG CTGGCGTTTT TCCATAGGCT CCGCCCCCCT      3360

GACGAGCATC ACAAAAATCG ACGCTCAAGT CAGAGGTGGC GAAACCCGAC AGGACTATAA      3420

AGATACCAGG CGTTTCCCCC TGGAAGCTCC CTCGTGCGCT CTCCTGTTCC GACCCTGCCG      3480

CTTACCGGAT ACCTGTCCGC CTTTCTCCCT TCGGGAAGCG TGGCGCTTTC TCATAGCTCA      3540

CGCTGTAGGT ATCTCAGTTC GGTGTAGGTC GTTCGCTCCA AGCTGGGCTG TGTGCACGAA      3600

CCCCCCGTTC AGCCCGACCG CTGCGCCTTA TCCGGTAACT ATCGTCTTGA GTCCAACCCG      3660
```

```
GTAAGACACG ACTTATCGCC ACTGGCAGCA GCCACTGGTA ACAGGATTAG CAGAGCGAGG    3720

TATGTAGGCG GTGCTACAGA GTTCTTGAAG TGGTGGCCTA ACTACGGCTA CACTAGAAGG    3780

ACAGTATTTG GTATCTGCGC TCTGCTGAAG CCAGTTACCT TCGGAAAAAG AGTTGGTAGC    3840

TCTTGATCCG GCAAACAAAC CACCGCTGGT AGCGGTGGTT TTTTTGTTTG CAAGCAGCAG    3900

ATTACGCGCA GAAAAAAAGG ATCTCAAGAA GATCCTTTGA TCTTTTCTAC GGGGTCTGAC    3960

GCTCAGTGGA ACGAAAACTC ACGTTAAGGG ATTTTGGTCA TGAGATTATC AAAAAGGATC    4020

TTCACCTAGA TCCTTTTAAA TTAAAAATGA AGTTTTAAAT CAATCTAAAG TATATATGAG    4080

TAAACTTGGT CTGACAGTTA CCAATGCTTA ATCAGTGAGG CACCTATCTC AGCGATCTGT    4140

CTATTTCGTT CATCCATAGT TGCCTGACTC CCCGTCGTGT AGATAACTAC GATACGGGAG    4200

GGCTTACCAT CTGGCCCCAG TGCTGCAATG ATACCGATTA TTGAAGCATT TATCAGGGTT    4260

ATTGTCTCAT GAGCGGATAC ATATTTGAAT GTATTTAGAA AAATAAACAA ATAGGGGTTC    4320

CGCGCACATT TCCCCGAAAA GTGCCACCTG GGTCCTTTTC ATCACGTGCT ATAAAAATAA    4380

TTATAATTTA AATTTTTTAA TATAAATATA TAAATTAAAA ATAGAAAGTA AAAAAAGAAA    4440

TTAAAGAAAA AATAGTTTTT GTTTTCCGAA GATGTAAAAG ACTCTAGGGG GATCGCCAAC    4500

AAATACTACC TTTTATCTTG CTCTTCCTGC TCTCAGGTAT TAATGCCGAA TTGTTTCATC    4560

TTGTCTGTGT AGAAGACCAC ACACGAAAAT CCTGTGATTT TACATTTTAC TTATCGTTAA    4620

TCGAATGTAT ATCTATTTAA TCTGCTTTTC TTGTCTAATA AATATATATG TAAAGTACGC    4680

TTTTTGTTGA AATTTTTTAA ACCTTTGTTT ATTTTTTTTT CTTCATTCCG TAACTCTTCT    4740

ACCTTCTTTA TTTACTTTCT AAAATCCAAA TACAAAACAT AAAAATAAAT AAACACAGAG    4800

TAAATTCCCA AATTATTCCA TCATTAAAAG ATACGAGGCG CGTGTAAGTT ACAGGCAAGC    4860

GATCCGTCCT AAGAAACCAT TATTATCATG ACATTAACCT ATAAAAATAG GCGTATCACG    4920

AGGCCCTTTC GTC                                                     4933
```

(2) INFORMATION FOR SEQ ID NO:3:

(i) SEQUENCE CHARACTERISTICS:
        (A) LENGTH: 864 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: PART (xi) SEQUENCE DESCRIPTION: SEQ ID NO:3:

```
TGTTCACCGC GGTGGCGGCC GCTCTAGAAC TAGTGGATCC TGCAAGCAGG ATAGACGGCA     60

TGCACGATTT GTAATAACAG AGTGTCTTGT ATTTTTAAAG AAAGTCTATT TAATACAAGT    120

GATTATATTA ATTAACGGTA AGCATCAGCG GGTGACAAAA CGAGCATGCT TACTAATAAA    180

ATGTTAACCT CTGAGGAAGA ATTGTGAAAC TATCACTAAT GGTAGCTATA TCGAAGAATG    240

GAGTTATCGG GAATGGCCCT GATATTCCAT GGAGTGCCAA AGGTGAACAG CTCCTGTTTA    300

AAGCTATTAC CTATAACCAA TGGCTGTTGG TTGGACGCAA GACTTTTGAA TCAATGGGAG    360

CATTACCCAA CCGAAAGTAT GCGGTCGTAA CACGTTCAAG TTTTACATCT GACAATGAGA    420

ACGTATTGAT CTTTCCATCA ATTAAAGATG CTTTAACCAA CCTAAAGAAA ATAACGGATC    480
```

```
ATGTCATTGT TTCAGGTGGT GGGGAGATAT ACAAAAGCCT GATCGATCAA GTAGATACAC        540

TACATATATC TACAATAGAC ATCGAGCCGG AAGGTGATGT TTACTTTCCT GAAATCCCCA        600

GCAATTTTAG GCCAGTTTTT ACCCAAGACT TCGCCTCTAA CATAAATTAT AGTTACCAAA        660

TCTGGCAAAA GGGTTAACAA GTGGCAGCAA CGGATTCGCA AACCTGTCAC GCCTTTTGTG        720

CCAAAAGCCG CGCCAGGTTT GCGATCCGCT GTGCCAGGCG TTAGGCGTCA TATGAAGATT        780

TCGGTGATCC CTGAGCAGGT GGCGGAAACA TTGGATGCTG AGAATTCGAT ATCAAGCTTA        840

TCGATACCGT CGACCTCGAG AACA                                              864

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: JB563

(xi) SEQUENCE DESCRIPTION: SEQ ID NO:4:

GACACTCTGT TATTACAAAT CG                                                 22

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: JB532

(xi) SEQUENCE DESCRIPTION: SEQ ID NO:5:

GGTGATCCCT GAGCAGGTGG                                                    20

(2) INFORMATION FOR SEQ ID NO:6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: JB661

(xi) SEQUENCE DESCRIPTION: SEQ ID NO:6:

AAAAGCTGGG TACCGAACAT GTTCTCGAGG TCGACGGTAT CG                           42
```

(2) INFORMATION FOR SEQ ID NO:7:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vii) IMMEDIATE SOURCE:
        (B) CLONE: JB662

(xi) SEQUENCE DESCRIPTION: SEQ ID NO:7:

GCGAATTGGA GCTCGAACAT GTTCACCGCG GTGGCGGCCG CTC          43